(12) United States Patent
Biberger et al.

(10) Patent No.: US 7,409,853 B2
(45) Date of Patent: Aug. 12, 2008

(54) FLOATABLE HOUSING FOR IN SITU WATER MONITORING SYSTEM

(75) Inventors: Maximilian A. Biberger, Scottsdale, AZ (US); Michael Lee Manasco, Tempe, AZ (US)

(73) Assignee: Hitek Aqua Systems, LLC, Tempe, AZ (US)

( * ) Notice: Subject to any disclaimer, the term of this patent is extended or adjusted under 35 U.S.C. 154(b) by 0 days.

(21) Appl. No.: 11/477,701

(22) Filed: Jun. 28, 2006

(65) Prior Publication Data

US 2007/0013381 A1    Jan. 18, 2007

Related U.S. Application Data

(60) Provisional application No. 60/696,081, filed on Jun. 30, 2005.

(51) Int. Cl.
*G01N 27/26* (2006.01)
*G01N 27/27* (2006.01)
*G01N 33/18* (2006.01)

(52) U.S. Cl. ............ 73/61.51; 73/61.41; 73/61.61; 73/61.71; 210/96.1; 340/539.22; 340/539.24; 340/539.26; 374/156

(58) Field of Classification Search ............ 73/53.01, 73/61.41–61.51, 61.61, 61.71, 431; 4/490; 210/85–95, 96.1; 374/156; 340/539.22, 340/539.24, 539.26
See application file for complete search history.

(56) References Cited

U.S. PATENT DOCUMENTS

| | | | | |
|---|---|---|---|---|
| 4,435,095 A | * | 3/1984 | Jones et al. | 374/194 |
| 4,510,487 A | | 4/1985 | Wolfe et al. | 340/566 |
| 4,781,810 A | * | 11/1988 | Tucker | 204/228.2 |
| 4,900,432 A | * | 2/1990 | Arnold et al. | 210/91 |
| 4,940,946 A | * | 7/1990 | Nazaryan | 324/438 |
| 5,115,222 A | * | 5/1992 | Peralta et al. | 340/573.6 |
| 5,124,960 A | * | 6/1992 | Miller et al. | 368/278 |
| 5,152,610 A | * | 10/1992 | Hallett | 374/156 |
| 5,169,236 A | * | 12/1992 | Iest | 374/156 |
| 5,189,350 A | * | 2/1993 | Mallett | 318/434 |
| 5,422,014 A | | 6/1995 | Allen et al. | 210/743 |
| 5,518,635 A | * | 5/1996 | Kohlman | 210/749 |
| 5,681,110 A | | 10/1997 | Burzacchi | 374/156 |
| 5,788,826 A | | 8/1998 | Nyberg | 204/536 |

(Continued)

FOREIGN PATENT DOCUMENTS

DE    199 21 436 A1    5/2000

(Continued)

*Primary Examiner*—Hezron E. Williams
*Assistant Examiner*—David A. Rogers
(74) *Attorney, Agent, or Firm*—Haverstock & Owens LLP

(57) ABSTRACT

An electronic system for use in a body of fluid is disclosed. The electronic system includes a first housing element and a second housing element. The second housing element is hermetically sealed to the first housing element, forming a first chamber there between. An electronic circuit is mounted within the first chamber. The electronic system further includes a second chamber internal to the second housing element. The second chamber is configured for holding a power source for the electronic circuit. Preferably, the power source is a battery pack. Also, the electronic system includes means for temporarily sealing the second chamber. Preferably, means for temporarily sealing the second chamber includes a detachable plug configured for coupling to the second housing element.

16 Claims, 24 Drawing Sheets

U.S. PATENT DOCUMENTS

| | | | |
|---|---|---|---|
| 5,996,138 A * | 12/1999 | Kentch | 4/508 |
| 6,113,858 A * | 9/2000 | Tang et al. | 422/82.09 |
| 6,223,359 B1 * | 5/2001 | Oltmanns et al. | 4/508 |
| 6,225,900 B1 * | 5/2001 | Keon et al. | 340/539.26 |
| 6,228,272 B1 * | 5/2001 | Gola | 210/742 |
| 6,238,553 B1 * | 5/2001 | Lin | 210/94 |
| 6,294,086 B1 * | 9/2001 | Reeves | 210/198.1 |
| 6,309,538 B1 * | 10/2001 | Khan | 210/85 |
| 6,340,431 B2 | 1/2002 | Khan | 210/85 |
| 6,476,721 B1 | 11/2002 | Diebold | 340/573.6 |
| 6,579,446 B1 | 6/2003 | Teran et al. | 210/85 |
| 6,653,842 B2 | 11/2003 | Mosley et al. | 324/446 |
| 6,697,706 B2 | 2/2004 | Gardner, Jr. | 700/244 |
| 6,713,298 B2 | 3/2004 | McDevitt et al. | 435/287.8 |
| 6,792,956 B2 * | 9/2004 | Bredo et al. | 134/22.18 |
| 6,958,693 B2 * | 10/2005 | Rothgeb et al. | 340/539.22 |
| 7,037,038 B1 * | 5/2006 | Haski et al. | 405/60 |
| 2001/0045380 A1 * | 11/2001 | Khan | 210/85 |
| 2002/0035403 A1 | 3/2002 | Clark et al. | 700/65 |
| 2003/0227394 A1 | 12/2003 | Rothgeb et al. | 340/870.01 |
| 2004/0031329 A1 * | 2/2004 | Carpenter et al. | 73/861.19 |
| 2004/0066313 A1 * | 4/2004 | Ong et al. | 340/870.11 |
| 2004/0208499 A1 * | 10/2004 | Grober | 396/428 |
| 2005/0220169 A1 * | 10/2005 | McGowan-Scanlon | 374/156 |
| 2005/0225766 A1 * | 10/2005 | Hansen et al. | 356/436 |
| 2005/0279677 A1 * | 12/2005 | Lin | 210/96.1 |

FOREIGN PATENT DOCUMENTS

| | | |
|---|---|---|
| WO | WO 03/087501 A1 | 10/2003 |
| WO | WO 03/091668 A2 | 11/2003 |

* cited by examiner

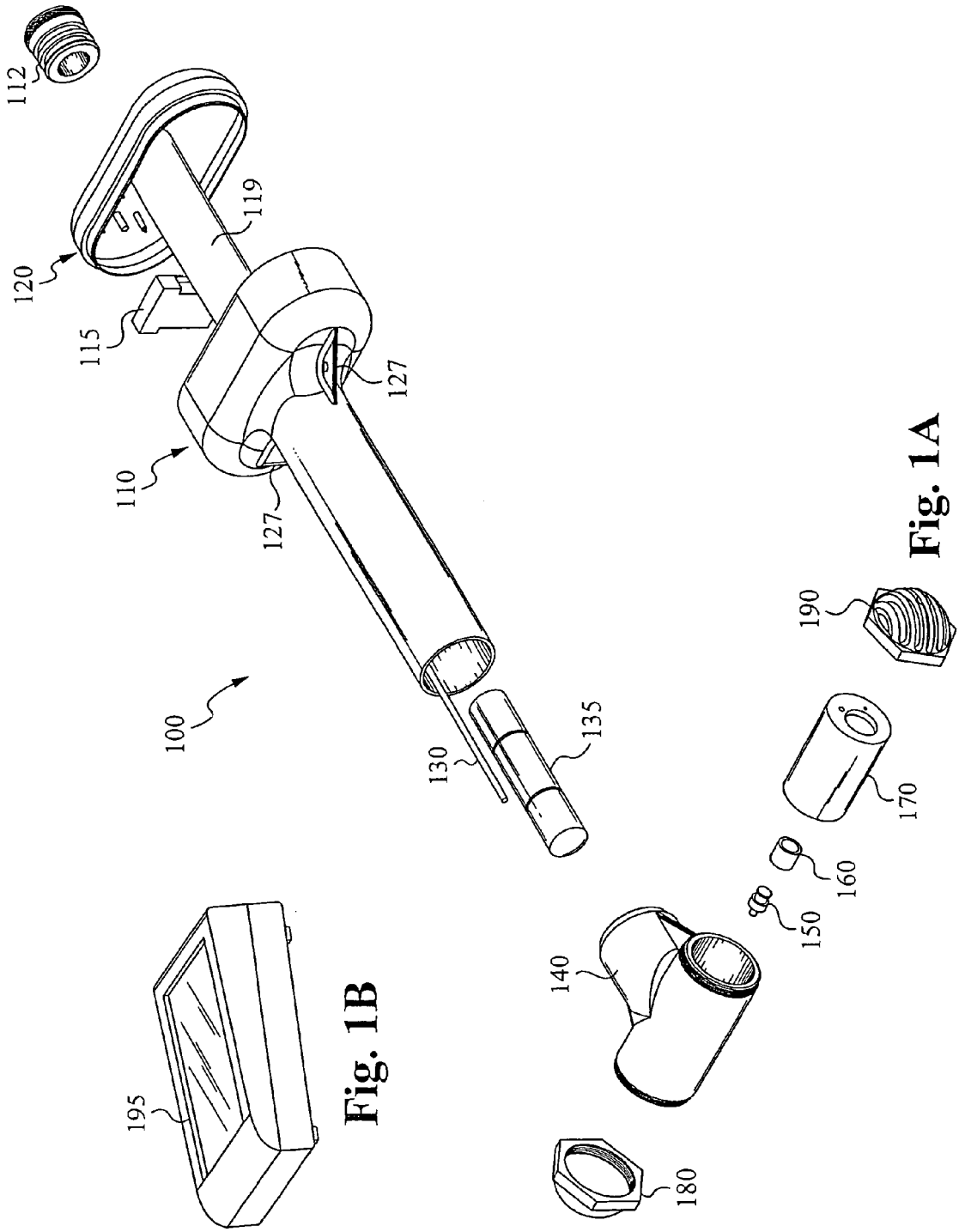

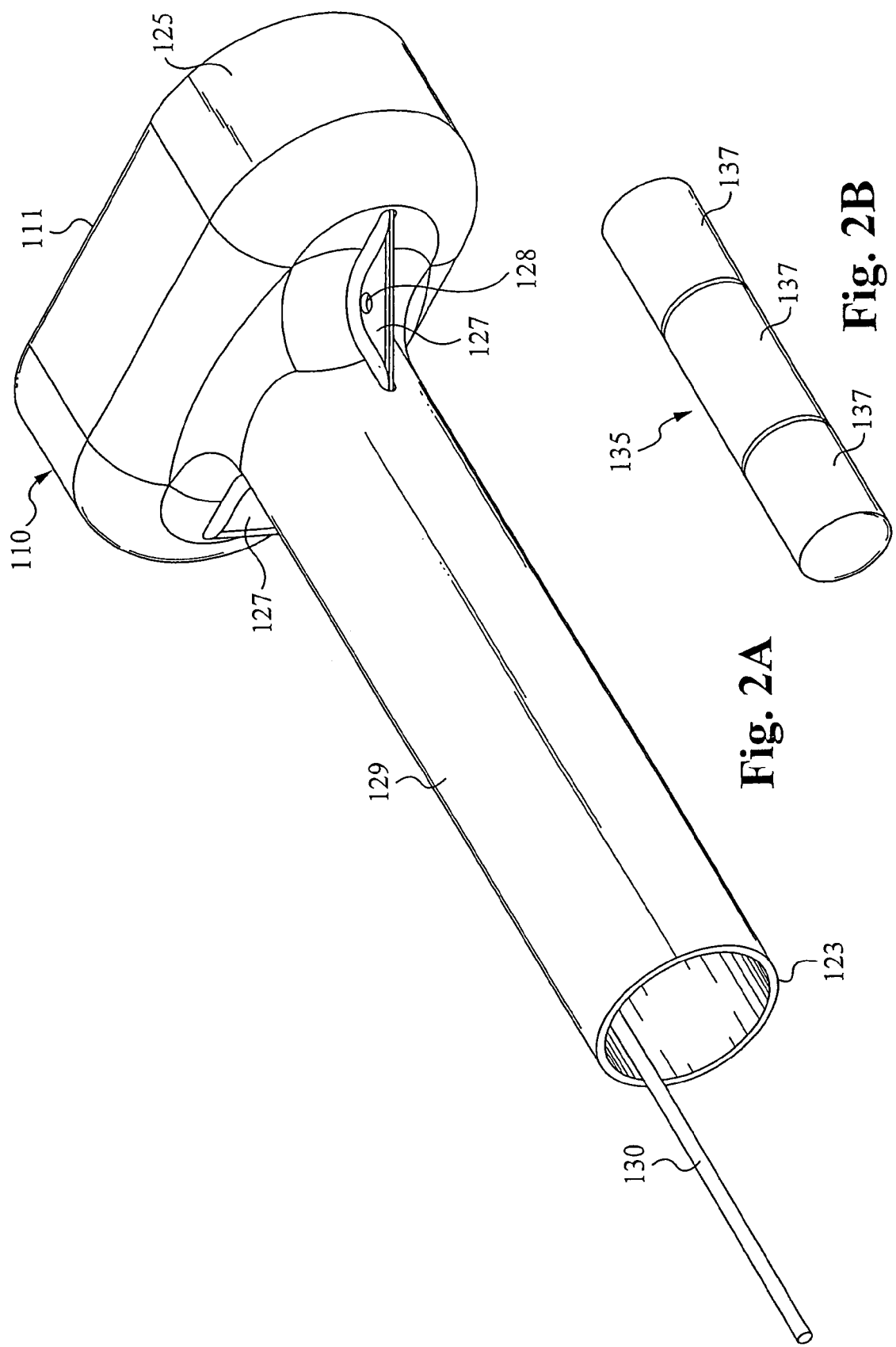

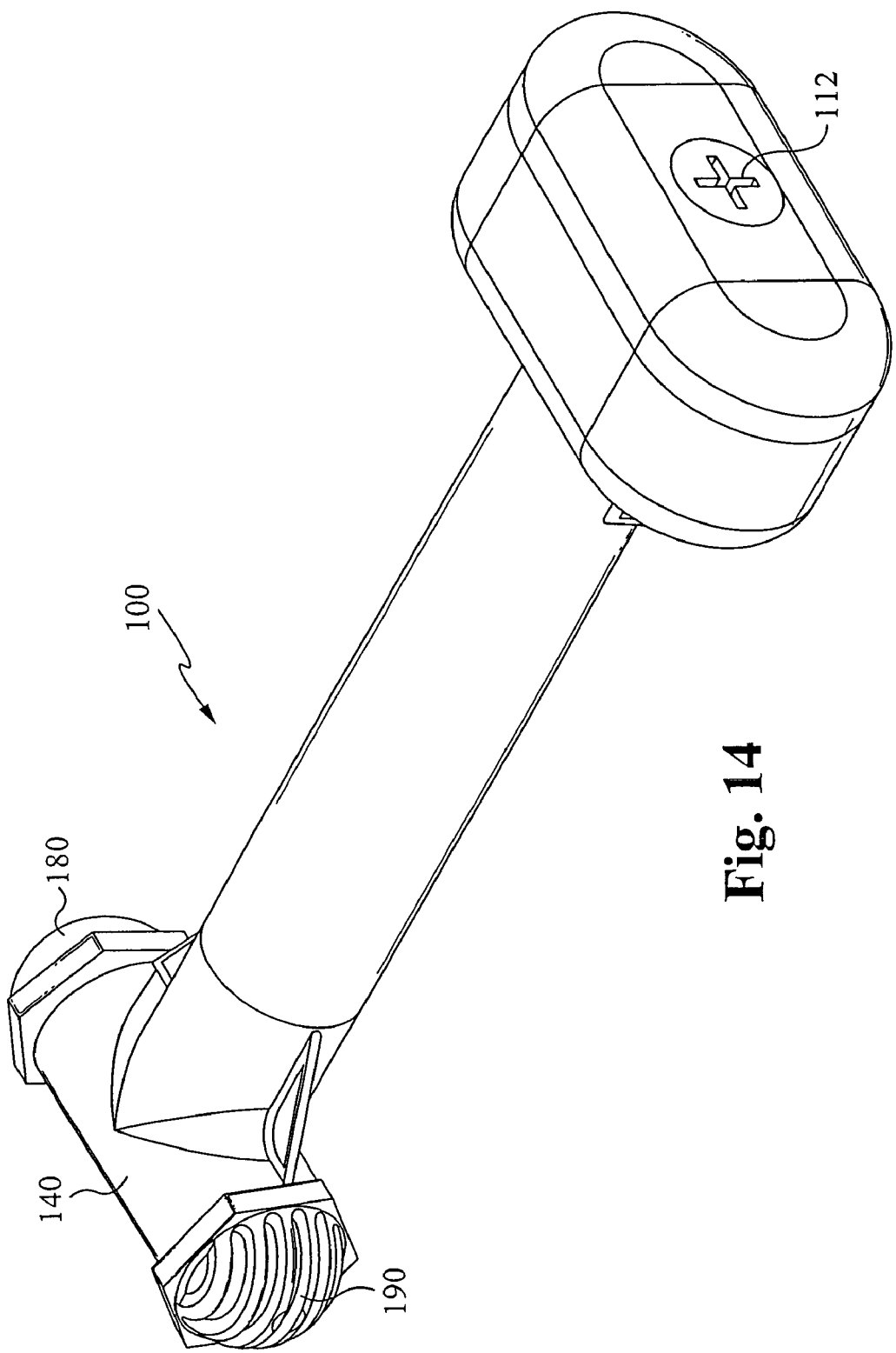

FLOATABLE HOUSING FOR IN SITU WATER MONITORING SYSTEM

RELATED APPLICATIONS

This application claims priority under 35 U.S.C. §119(e) to co-pending U.S. Provisional Application Ser. No. 60/696,081, filed Jun. 30, 2005, entitled "IN-SITU WATER ANALYSIS METHOD AND SYSTEM," the entirety of which is hereby incorporated by reference as if set forth herein. This application also claims priority under 35 U.S.C. §120 to co-pending U.S. Utility application Ser. No. 11/165,478, filed Jun. 22, 2005, entitled "IN-SITU WATER ANALYSIS METHOD AND SYSTEM." the entirety of which is hereby incorporated by reference as if set forth herein.

FIELD OF INVENTION

The present invention relates generally to the field of water analysis. More specifically, the present invention relates to the field of automated water chemistry analysis.

BACKGROUND OF THE INVENTION

For owners of recreational aquatic facilities, such as pools, spas, and hot tubs, water chemistry must be properly maintained to deflect the hazards associated with water not properly balanced. If the chemistry of a pool is even slightly off, for instance, a serious health hazard can be posed to users. Also, water that is not properly balanced can result in a quick deterioration of an aquatic facility, resulting in expensive rehabilitation costs.

Presently, water chemistry can be checked by chemistry kits, laboratory runs, and maintenance service calls. Although chemistry kits are typically less expensive than maintenance service calls, most chemistry kits are messy, complicated, and are not user-friendly. Even if one knows how to properly use a chemistry kit, that individual may be uncertain of the results, thereby necessitating a double check of the water chemistry through a laboratory run such as to a swimming pool supply store.

A laboratory run requires the taking of a sample of water for a chemistry laboratory to analyze. Traveling to and from a laboratory with the sample during normal business hours is inconvenient. Further the result is obtained after a significant lag time has elapsed. Moreover, the analysis of water chemistry and an evaluation of the amount of additives to remedy any perceived imbalance is a function of water temperature. It is almost certain that the temperature of the sample will change in transit to the laboratory. Furthermore, once the results are received from a laboratory, water chemistry may have changed and as a consequence, one may be relying on an inaccurate water chemistry reading. For those who use chemistry kits and laboratory runs, both options also do not address the problem of physically adding chemicals to the water, which equate to an added inconvenience of releasing messy chemicals, without much assurance that the correct amount of chemicals are being released at the proper time. Overall, chemistry kits, laboratory runs, and adding chemicals on a do-it-yourself basis can be inaccurate, labor-intensive and time-consuming.

In contrast, maintenance service calls are expensive and inconvenient. Although service calls are typically conducted at regular intervals, sometimes maintenance service personnel are unavailable when their services are most needed, such as after a rain storm or before a pool party. Also, some maintenance service personnel are unreliable and/or careless in their methodology, forcing one to double check water chemistry by using a chemistry kit or a laboratory run. Finally, such service calls can be conducted by a variety of maintenance personnel, thereby increasing the likelihood of human error in monitoring and balancing water chemistry.

In our copending, co-owned patent application Ser. No. 11/165,478, filed Jun. 22, 2005 and entitled "IN-SITU WATER ANALYSIS METHOD AND SYSTEM, an electronic water monitoring and reporting system is disclosed. The system operates and performs the function for which it was intended. Because the system is intended to operate at least partially immersed in a body of water away from the electronic circuit to prevent damage. It is possible to place the engine unit into a water proof housing such as commonly used for other proof electronic devices. Periodically the housing must be opened to replace the battery. Each time the housing is re-closed special care is taken to ensure the seal is correctly formed. Failure to form an adequate seal in damage to the circuit. Also, failure to fully dry the unit prior to opening can allow water that remained on the outside of the housing or the user's hands to enter the housing and cause immediate or eventual damage to the circuit.

Electronic devices for water immersion are known. One example of such a device are radios. The electronic circuits and the battery system are contained within a single waterproof enclosure. When the batteries are required to be changed, the electronic circuit is exposed to the ambient and potentially to water. As is generally recognized, exposing electronic circuits will typically cause short circuits and can result in failure of the electronic circuit to operate and can further cause permanent damage.

What is needed is an immersible system for monitoring water chemistry which is battery operated. What is further needed is an immersible system for monitoring water chemistry which includes means to replace batteries without exposing the electronic circuitry to water or the ambient.

What is needed is a safe, convenient, user-friendly automated system for monitoring water chemistry.

What is needed is an efficient, time-sensitive automated system for both monitoring water chemistry and adding necessary chemicals to balance the water.

What is needed is a reliable automated method for monitoring water chemistry.

What is needed is a secure, dependable automated method for both monitoring water chemistry and adding appropriate chemicals to maintain the balance of a body of water.

BRIEF SUMMARY OF THE INVENTION

The present invention provides for an electronic system for use in a body of fluid. Preferably, the system automatically monitors water chemistry of a body of water. Preferably, the system simultaneously monitors the pH level, temperature, and chlorine of a pool on site, thereby ensuring the reliability and timeliness of the pool water chemistry readings taken by the system. Preferably, the system is floatable and can be tethered. The present invention is further configured to hermetically seal certain components of the system, such that these components are protected from moisture and other environmental elements which could otherwise hamper the ability of the system to accurately monitor water chemistry of the pool.

A first aspect of the invention is for an electronic system for use in a body of fluid. Preferably, the body of fluid includes a pool, such as a residential or commercial pool. Preferably, the electronic system is floatable in the body of fluid and is configured to be selectively tethered. The electronic system includes a first housing element and a second housing element. The second housing element is hermetically sealed to the first housing element, forming a first chamber there between. Further, an electronic circuit is mounted within the first chamber. The electronic system includes a second chamber internal to the second housing element. The second chamber is configured for holding a power source for the electronic circuit. Preferably, the power source is a battery pack. Also, the electronic system includes means for temporarily sealing the second chamber. Preferably, means for temporarily sealing the second chamber includes a detachable plug configured for coupling to the second housing element. The electronic circuit preferably includes a transmitter configured to transmit through a radio connection.

A second aspect of the invention is for a device to remotely monitor a body of fluid. The device includes an electronic circuit and a display. The electronic circuit is configured for receiving information from a remote transmitter and processing the information. The display is for displaying the information received and processed by the electronic circuit. Preferably, the electronic circuit comprises a microprocessor. Preferably, the electronic circuit is paired to receive information only from a designated remote transmitter. The designated remote transmitter likewise has been programmed to transmit only to the electronic circuit in the device.

A third aspect of the invention is a method for manufacturing an electronic system having a first housing element and a second housing element, where the electronic system is for use in a body of fluid. The method includes hermetically sealing the second housing element to the first housing element, thus forming a first chamber there between. The method further includes mounting an electronic circuit within the first chamber and configuring a second chamber internal to the second housing element, for holding a power source for the electronic circuit. The method preferably also includes temporarily sealing the second chamber. Preferably, the second chamber is sealed using a plug.

BRIEF DESCRIPTION OF THE DRAWINGS

FIG. 1A is a schematic exploded drawing of a overall front isometric view of an electronic system for use in a a body of fluid, in accordance with a preferred embodiment of the present invention.

FIG. 1B is a schematic drawing showing a handheld device configured to receive information from the electronic system of FIG. 1A.

FIG. 2A is a schematic drawing of an overall front isometric view of a first housing element and a cable of the electronic system of FIG. 1A, in accordance with the preferred embodiment.

FIG. 2B is a schematic drawing of an isometric view of a battery pack for the electronic system of FIG. 1A, in accordance with the preferred embodiment.

FIG. 7C is a schematic drawing of the sensor mount, the wetted cap and the storage cap.

FIG. 14 is an overall front isometric of the electronic system of FIG. 1A in complete assembly, in accordance with the preferred embodiment.

DETAILED DESCRIPTION OF THE PRESENT INVENTION

The present invention discloses an electronic system for use in a body of fluid, as well as a method of manufacturing such an electronic system. Preferably, the body of fluid is a pool. In accordance with the preferred embodiment, the present invention allows for water chemistry of a pool to be properly maintained without resorting to time-consuming lab tests, pH testing, and expensive water maintenance house calls from pool maintenance personnel. The electronic system preferably is configured to house and hermetically seal delicate electronic components, thereby allowing the electronic system to be used in a body of fluid without the danger of exposing the electronic components to potentially dangerous conditions external to the electronic system, such as moisture and adverse contact. The invention further allows for a pool to be monitored using a handheld or desk top device that has been configured to receive information transmitted from the electronic system in the body of fluid.

Figure 1C:
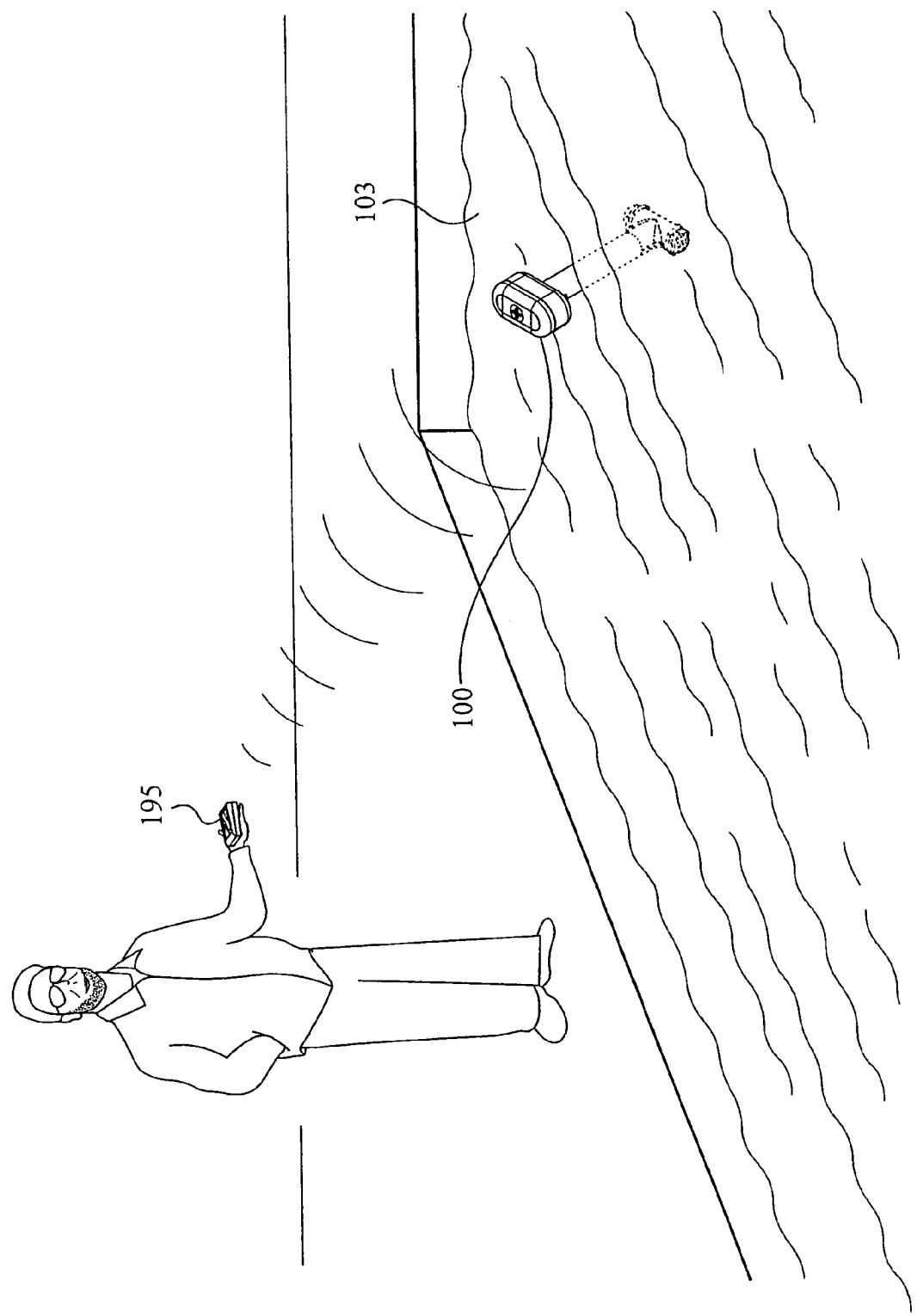
FIG. 1C is a schematic drawing showing the electronic system 100 of FIG. 1A for monitoring a pool in conjunction with the handheld device of FIG. 1B, in accordance with the preferred embodiment.

FIGS. 1A and 1C show an electronic system 100 for use in a body of fluid 103, in accordance with a preferred embodiment of the present invention. Preferably, the body of fluid 103 is a pool; however, the invention is not limited to pools only. The present invention encompasses all bodies of fluid, including but not limited to vats of fluid, tubs, containers of fluid, pools, spas, recreational aquatic facilities, hot tubs, whirlpool tubs, and the like. Preferably, the electronic system 100 is configured to float in the body of fluid 103, as shown in FIG. 1C. The electronic system 100 can be further configured to be tethered, which will be discussed later. However, it will be apparent to those skilled in the art that the electronic system 100 can also be configured to be mountable. Thus, the electronic system 100 can be mounted to a side, edge, wall, or surface of a pool, a vat, a tub, a container, a hot tub, a whirlpool tub, a spa, and the like, using a mounting element, such as a bracket.

Referring to FIG. 1A, the electronic system 100 preferably includes several elements. In FIG. 1A, the electronic system 100 is shown disassembled for the purpose of depicting each element in relation to the overall configuration of the electronic system 100 in accordance with the preferred embodiment. However, preferably, the complete assembly of the electronic system 100 is depicted in FIG. 14. It will be apparent to those skilled in the art that the accompanying figures are exemplary only. The electronic system 100 can be in any shape, size, manner, color form, and dimension, without departing from the scope of the present invention.

Preferably, the electronic system 100 includes a first housing element 110 and a second housing element 120. Initially, during manufacturing, the first housing element 110 and the second housing element 120 are formed separately and are therefore detachable. Preferably, the first housing element 110 and the second housing element 120 are injection molded or resin molded. This allows for the first housing element 110 and the second housing element 120 to be durable and long lasting, thereby increasing the longevity of the electronic system 100. Preferably during the manufacturing stage, the second housing element 120 is hermetically sealed to the first housing element 110, thereby forming a first chamber between the first housing element 110 and the second housing element 120.

Figure 4:
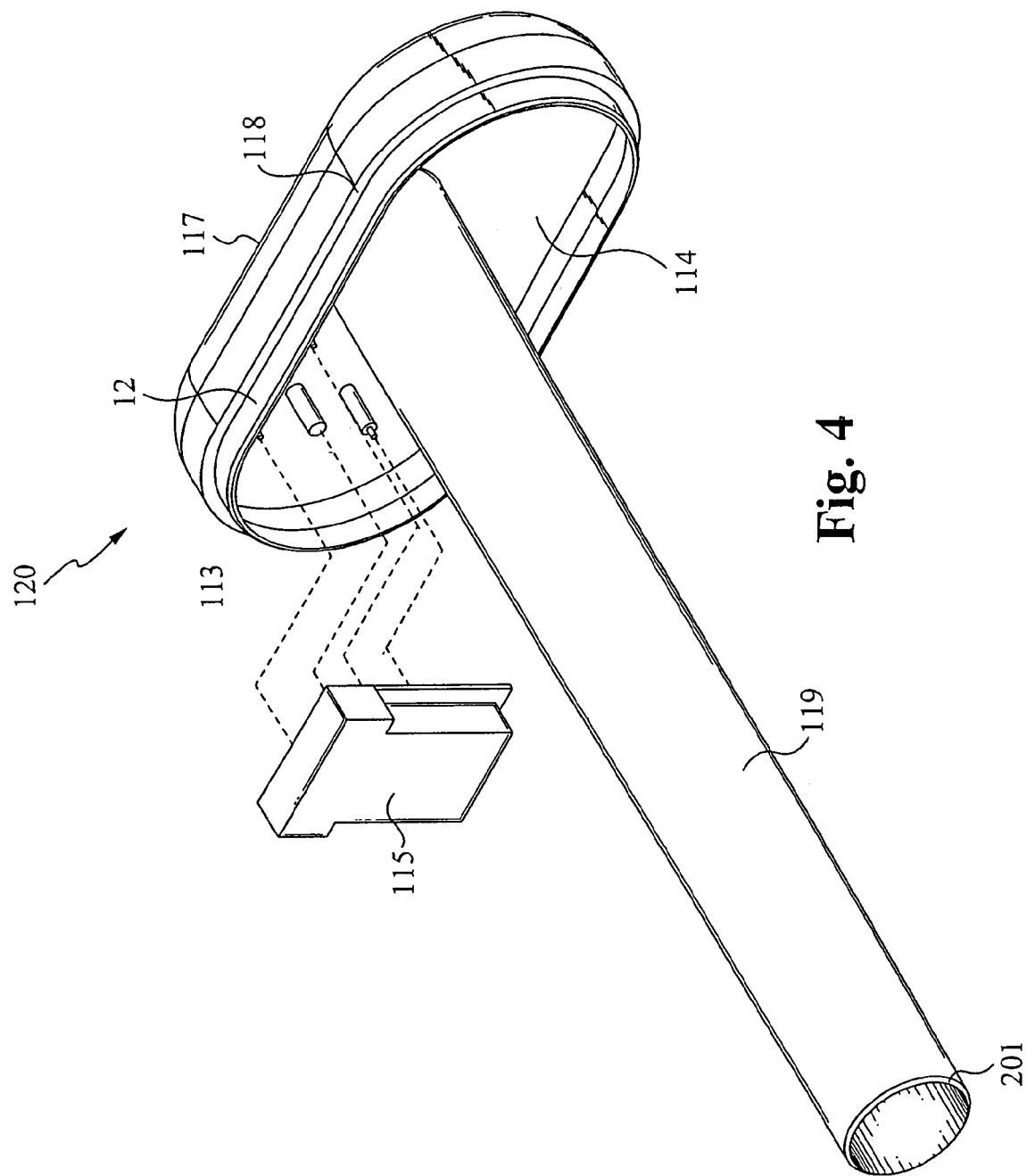
FIG. 4 is a schematic drawing of an enlarged front isometric view of a second housing element and a transmitter board of the electronic system of FIG. 1A, in accordance with the preferred embodiment.

Preferably, the second housing element 120 is hermetically sealed to the first housing element 110 using a watertight, anti-moisture sealant, glue, epoxy or the like that is applied to both the first housing element 110 and the second housing element 120, which will discussed further in a latter portion of this document. The sealant eliminates the possibility of water moisture and other external conditions from invading, seeping in, or penetrating the first chamber between the first housing element 110 and the second housing element 120. This in turn permanently protects the electronic circuit 115 which is mounted within the first chamber, preferably mounted with four mounting elements 113 as shown in FIG. 4. Still referring to FIG. 1A, preferably, the electronic circuit 115 includes a transmitter for transmitting chemistry information for the body of fluid 103 (FIG. 1C) to a device 195 (FIGS. 1B and 1C). The device 195 can be one of a portable device, a handheld device, a personal digital assistant (PDA), a computer, a wireless device, a phone, and any combination of at least two thereof. By hermetically sealing the second housing element 120 to the first housing element 110, the contents of the first chamber (namely, the electronic circuit 115 and the cable 130) are impervious to moisture, fluid, and other external conditions, such as wind, air, and outside sources.

Figure 15:
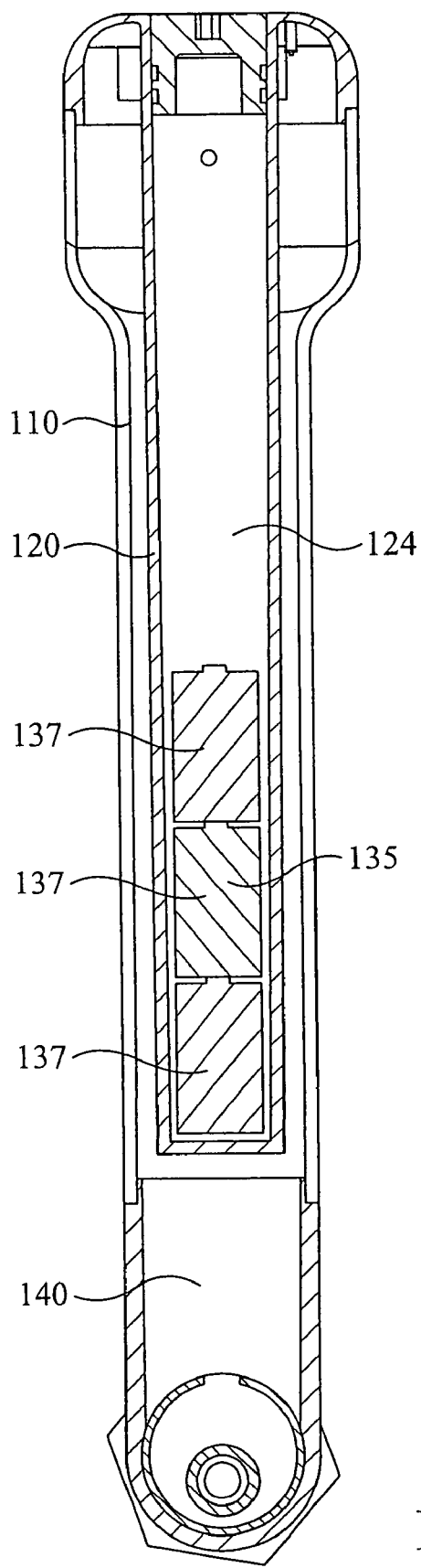
FIG. 15 is a schematic drawing of a side cross-sectional interior view of the electronic system of FIG. 1A, in accordance with the preferred embodiment of the present invention.

The electronic system 100 further includes a second chamber. The second chamber is internal to the second housing element 120 and it is configured for holding a power source for the electronic circuit 115. Preferably, the second chamber is internal to a cylindrical member 119 (FIG. 4) of the second housing element 120; Preferably, the power source includes a battery pack 135 of three DC batteries 137, as depicted in FIGS. 2B and 15. As shown in FIG. 15, preferably, the cylindrical member 119 of the second housing element 120 includes a hollow interior chamber configured to house the battery pack 135. The electronic system 100 also includes means for temporarily hermetically sealing the second chamber. Preferably, the means for temporarily hermetically sealing the second chamber includes a detachable battery plug 112 (FIG. 1) configured to couple to the second housing element 120. This too shall be discussed in greater detail later herein.

Figure 3:
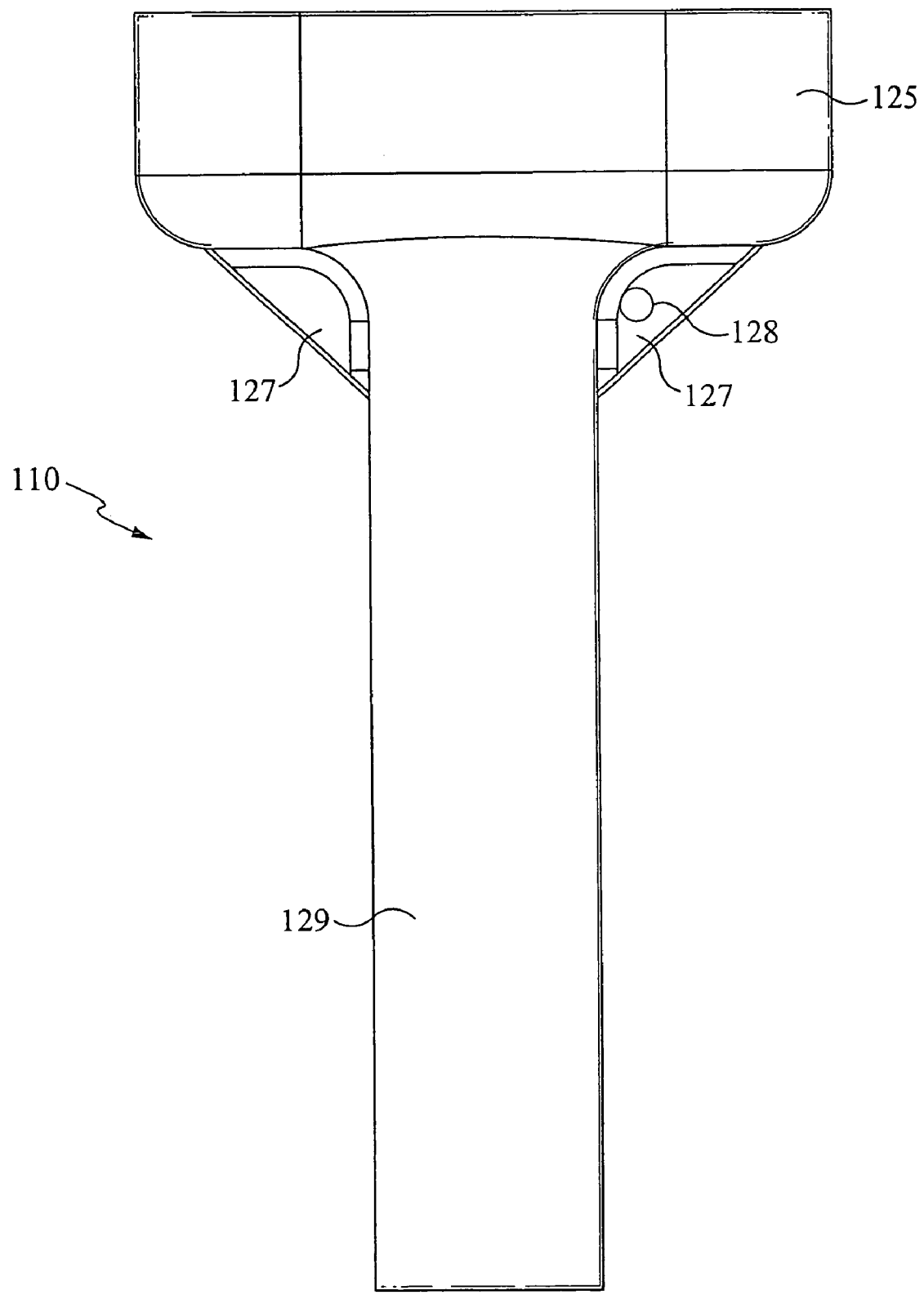
FIG. 3 is a schematic drawing of a front view of the first housing element of the electronic system of FIG. 1A, in accordance with the preferred embodiment.

FIGS. 2A and 3 show the first housing element 110 in an overall isometric view and an elevational front view, respectively. The first housing element 110 preferably has a first cylindrical member 129 and an upper portion 125. The first cylindrical member 129 of the first housing element 110 is preferably configured to enclose or surround a second cylindrical member 119 (FIG. 4) of the second housing element 120. Preferably, the second cylindrical member 119 of the second housing element 120 is smaller in diameter and/or shorter in length than the first cylindrical member 129 of the first housing element 110. Preferably, this is done in a manner such that the first cylindrical member 129 of the first housing element 110 acts like a sheath to the second cylindrical member 119 (FIG. 4) of the second housing element 120. Also, preferably, the first cylindrical member 129 of the first housing element 110 is configured to house a cable 130 configured to couple the electronic circuit 115 (FIG. 1) to the sensor (not shown) in the sensor mount 140 (FIG. 1).

Still referring to FIGS. 2A and 3, the upper portion 125 of the first housing element 110 further includes an edge 111 configured to couple to a skirt 12 (FIG. 4) of the second housing element 120. Preferably, the edge 111 of the first housing element 110 (FIG. 2A) and the skirt 12 of the second housing element 120 are configured to couple, such that an anti-moisture sealant, plastic glue, or epoxy can be applied to both the edge 111 and the skirt 12, thereby hermetically sealing the second housing element 120 to the first housing element 110. Preferably, an epoxy adhesive or a plastic glue is applied to both the edge 111 and the skirt 12, thereby hermetically sealing the first chamber between the first and second housing elements 110 and 120. The skirt 12 aids in the hermetic seal, since the wall dimensions of the skirt 12 provide an ample sealing surface to make contact with the edge 111. This ensures a watertight seal for the first chamber between the first housing element 110 and the second housing element 120 (FIG. 1A).

Preferably, the first housing element 110 in FIG. 2A also includes two support members 127. The support members 127 are configured to support and couple the upper portion 125 to the cylindrical member 129 of the first housing element 110. Preferably, at least one of the support members 127 has an aperture 128 for a tether. Thus, the electronic system 100 (FIG. 1A) can be configured for tethering. The first housing element 110 also includes an end 123 for coupling the sensor mount 140 (FIG. 1) to the first housing element 110. Preferably the end 123 is also hermetically sealed to the sensor mount 140 (FIG. 1) by applying an anti-moisture epoxy, glue, or sealant where the end 123 and the sensor mount 140 are joined.

Figure 5:
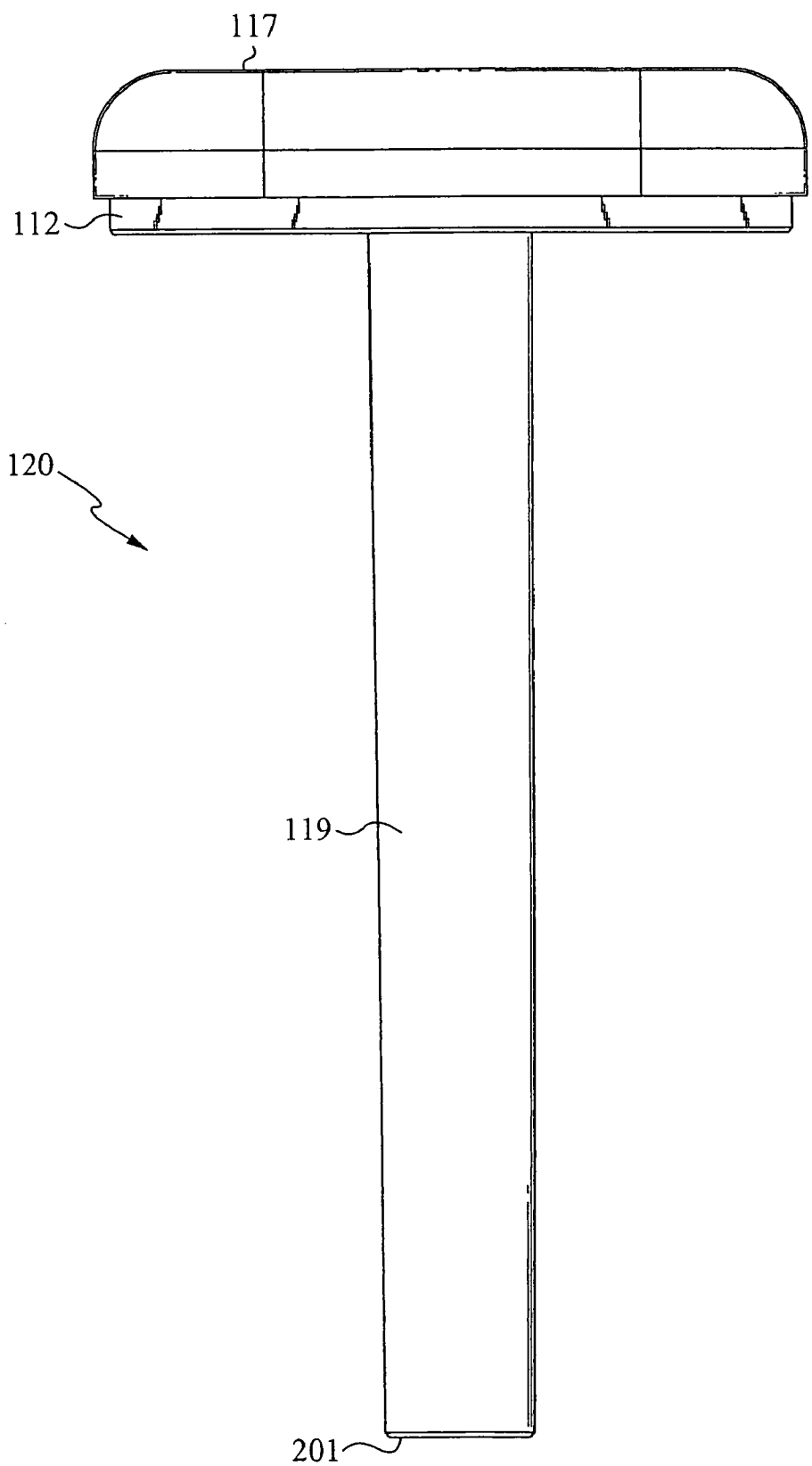
FIG. 5 is a schematic drawing of a front view of the second housing element of the electronic system of FIG. 1A, in accordance with the preferred embodiment.

FIGS. 4 and 5 show the second housing element 120 having a skirt 12 and a second cylindrical member 119. Preferably, the second cylindrical member 119 includes a smaller diameter and/or shorter length than the first cylindrical member 129 (FIG. 2A) of the first housing element 110. As previously discussed, this allows for the first cylindrical member 129 (FIG. 2A) of the first housing element 110 to sheath or enclose the second cylindrical member 119 (FIGS. 4 and 5) of the second housing element 120. Referring still to FIG. 4, the skirt 12 of the second housing element 120 preferably includes at least one o-ring 118. The skirt 12 is configured to couple with the first housing element 120 (FIG. 1A). Preferably, the skirt 12 of the second housing element 120 is configured to couple to the edge 111 of the first housing element 110, such that a sealant, glue, or epoxy can be applied to both the skirt 116 and the edge 111, thereby hermetically sealing the second housing element 120 to the first housing element 110. The second housing element 120 further includes a top 117 and an underside 114. The underside 114 preferably includes four mounting elements 113 to mount the electronic circuit 115 within the first chamber between the first housing element 110 (FIG. 1A) and the second housing element 120. Preferably, the electronic circuit 115 includes a transmitter board configured to be mounted onto the underside 114 of the second housing element 120 using screws (not shown) and mounting elements 114. The four mounting elements 113 preferably are coupled to the second housing element 120, but the present invention encompasses the mounting elements 113 to be on the first housing element 110 or both the first and second housing elements 110 and 120, so long as the electronic circuit 115 is mounted in the first chamber between the first and second housing elements 110 and 120. It will be apparent to those skilled in the art that the present invention encompasses any type of coupling element for coupling the electronic circuit 115 to the first and second housing elements 110 and 120. Thus, it is envisioned that the electronic circuit 115 can be coupled to any portion of the first and second housing elements 110 and 120, using any type, shape, size, and number(s) of coupling element, so long as the first and second housing elements 110 and 120 hermetically enclose the electronic circuit 115.

Still referring to FIGS. 4 and 5, the top 117 of the second housing element 120 includes an aperture or opening (not shown) to the second chamber internal to the second housing element 120. As discussed previously, the second housing element 120 preferably includes a second cylindrical member 119 configured for housing a power supply for the electronic circuit 115 (FIG. 1A). Preferably, the second cylindrical member 119 of the second housing element 120 has a smaller diameter and length than the first cylindrical member 129 of the first housing element 110 (FIG. 1A), such that the second cylindrical member 119 of the second housing element 120 is configured to enclose, protect, or sheath the first cylindrical member 129 of the first housing element 110. Preferably, when the first housing element 110 and the second housing element 120 are coupled and hermetically sealed in manufacturing, the second cylindrical member 119 of the second housing element 120 preferably encloses the entire length of the first cylindrical member 129 of the first housing element 110.

The second chamber is preferably inside the second cylindrical member 119 of the second housing element 120. The second chamber is further configured to house a power supply, preferably a battery pack 135 of three DC batteries 137, for the electronic circuit 115 (FIG. 1A). As shown in FIG. 15, the second chamber 124 houses three DC batteries 137, which are stacked end to end in the second chamber 124 shown in FIG. 15 inside the second housing element 120. However, the number of batteries 137 for the battery pack 135 and the configuration of those batteries 137 in the second chamber 124 is exemplary only. The present invention encompasses any number, size, type, combination, and/or configuration of batteries for the battery pack 135. Further, the present invention is not limited to having a battery pack 135 as a power supply for the electronic circuit 115 (FIG. 1A). The present invention can further encompass any type of power supply for the electronic circuit 115.

Preferably, the electronic system 100 (FIG. 1A) further includes a battery pigtail (not shown) for coupling the electronic circuit 115 to the battery pack 135. The battery pigtail goes from the electronic circuit 115 to the battery pack 135 through an opening (not shown) in the second cylindrical member 119 of the second housing element 120. Once the battery pigtail couples the electronic circuit 115 to the battery pack 135, at manufacturing, the opening (not shown) is hermetically sealed using an appropriate sealant, epoxy, or glue, to secure the battery pigtail in its place and to seal out any moisture.

Further, in accordance with the preferred embodiment, the electronic system 100 (FIG. 1A) includes means for temporarily hermetically sealing the second chamber internal to the second housing element 120. Preferably, the second chamber is temporarily hermetically sealed by a plug 112. Preferably, the plug 112 is a battery plug since in the preferred embodiment, the second chamber 124 (FIG. 15) is configured to house a battery pack 135. Thus, the battery plug 112 temporarily hermetically seals the battery pack 135. The battery plug 112 (FIG. 1A, 10A, 10B, and 10C) preferably is detachable from the second housing element 120. The battery plug 112 preferably includes a plurality of o-rings 204, a plurality of threads 77, a battery plug top 116, and a battery plug bottom 126. Preferably, the o-rings 204 and the threads 77 are on a surface of the battery plug 112 between the battery plug top 116 and the battery plug bottom 126. Preferably, the battery plug 112 contains at least two o-rings 204 and at least five threads 77, which make it extremely unlikely for fluid to bypass the battery plug 112 and enter into the second chamber. Preferably, the battery plug top 116 further includes a battery plug handle 88 (FIG. 10B) configured for handling the battery plug 112. Preferably, the battery plug handle 88 is configured to couple or decouple the battery plug 112 from the top 117 (FIG. 4) of the second housing element 120. Preferably, the battery plug handle 88 is configured for tactile grasping.

Figure 10A:
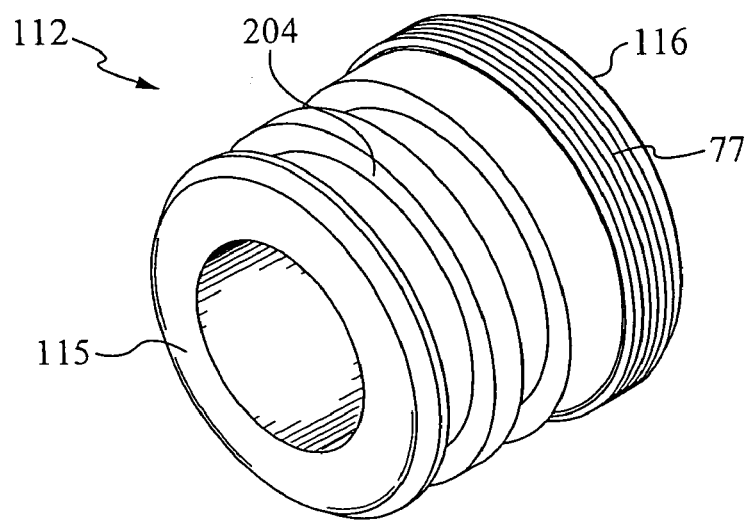
FIG. 10A is a schematic drawing of a perspective view of a battery plug for the electronic system of FIG. 1A, in accordance with the preferred embodiment.
Figure 10B:
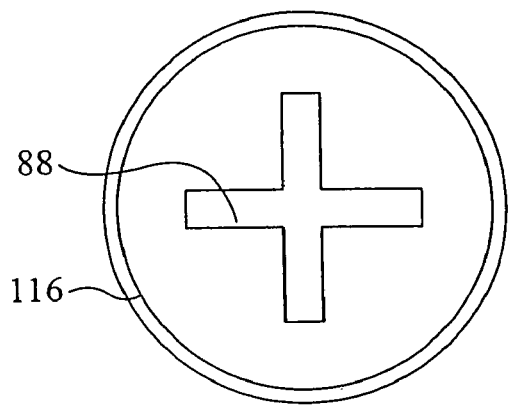
FIG. 10B is a schematic drawing of a side cross-sectional view of the battery plug of FIG. 10A.
Figure 10C:
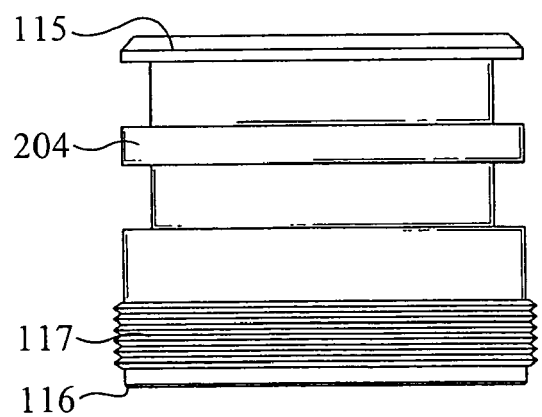
FIG. 10C is a schematic drawing of a front elevational view of the battery plug of FIG. 10A.
Figure 10D:
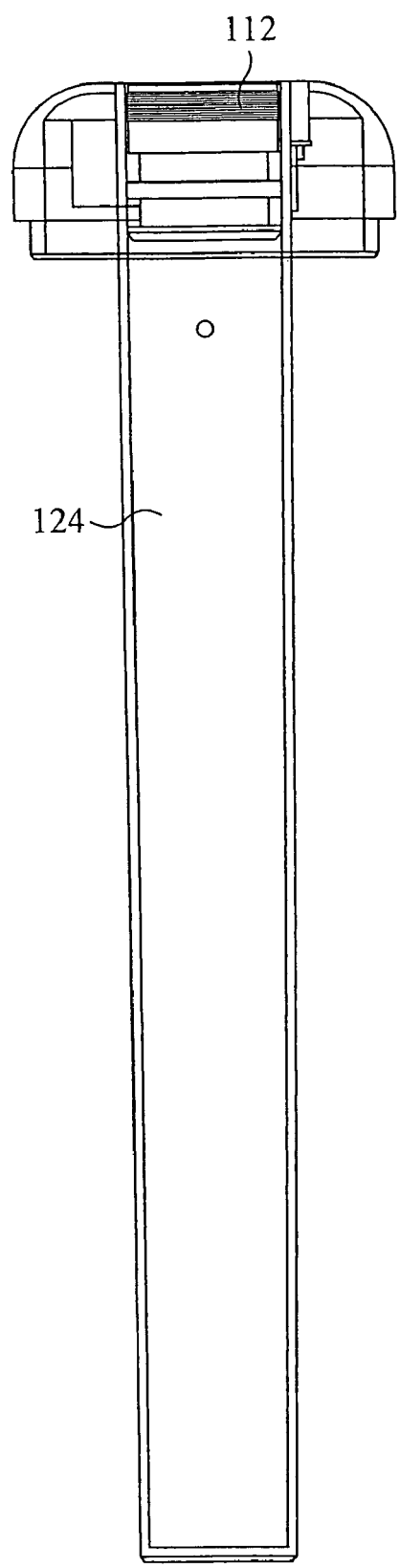
FIG. 10D is a schematic drawing of the battery plug hermetically sealing the second chamber of the electronic system of FIG. 1A, in accordance with the preferred embodiment.

As shown in FIGS. 1A and 10A, the battery plug 112 can be twisted, screwed in, turned, or otherwise coupled to the top 117 of the second housing element 120 through an aperture (not shown). The aperture preferably allows for access to the second chamber 124 (FIGS. 10D and 15) of the second cylindrical member 119 (FIG. 5) of the second housing element 120. Thus, the aperture of the second housing element 120 is the vehicle in which the battery plug 112 hermetically seals the second chamber 124. FIG. 10D shows the battery plug 112 hermetically sealing the second chamber 124. Later, the battery plug 112 can be used to unseal the second chamber by unscrewing or twisting the battery plug 112 from the aperture in the top 117 of the second housing element 120. If the battery plug 112 is decoupled or detached from the top 117 of the second housing element 120, the second chamber is no longer hermetically sealed though the first chamber remains hermetically sealed though the first chamber remains hermetically sealed. If the second chamber of the second housing element 120 is empty, then a battery pack 135 (FIG. 1A) can be inserted or pushed through the aperture of the second housing element 120. This allows for the battery pack 135 to enter into the second chamber, which preferably includes the interior of the second cylindrical member 119 of the second housing element 120. Then, the battery plug 112 can be once again screwed in or twisted onto the top 117 of the second housing element 120, thereby temporarily hermetically sealing the second chamber and the contents therein. The o-rings 204 and the threads 77 greatly enhance the ability of the plug 112 to hermetically seal the second chamber. Also, the battery plug 112 allows for the battery pack or the power supply 135 to be easily replaced, when the battery pack 135 fails or begins to corrode. When the battery pack 135 needs to be replaced, the electronic system 100 (FIG. 1A) is simply flipped upside down with the battery plug 112 detached, so that gravity will cause the battery pack 135 to exit the second chamber.

Returning to FIG. 1A, as previously discussed, the first cylindrical member 129 of the first housing element 110 preferably houses a cable 130. The cable 130 preferably couples the electronic circuit 115 to the sensor (not shown) housed inside the sensor mount 140. The cable 130 preferably includes a plurality of cable wires and the cable 130 includes a shielding. Preferably, the cable 130 includes five cable wires which are coupled to the electronic circuit 115. Preferably, the electronic circuit 115 is a transmitter board. The transmitter board 115 is cleaned and coated with an anti-moisture coating. The wires of the cable 130 are also soldered to the transmitter board 115. Thus, initially, one end of the cable 130 is coupled the transmitter board 115 and hangs or dangles from the transmitter board 115 through the first and second housing elements 110 and 120. Preferably, the cable 130 is housed in the first chamber, and is therefore hermetically sealed by the first and second housing elements 110 and 120. Preferably, the other end of the cable 130 is later coupled to the sensor (not shown) in the sensor module 170. The cable 130 is thus configured to transmit information sensed by the sensor (not shown) to the transmitter board 115.

Preferably a weight (not shown) is placed between the battery pack 135 and the sensor mount 140 of the electronic system 100 (FIG. 1A). Thus, the weight sits close to the bottom of the electronic system 100 and preferably sits on top of the sensor mount 140. Preferably, the weight weighs approximately 750 grams. However, the present invention is not limited to 750 gram weights and other weights having more or less mass can be used. The present invention encompasses any amount of weight, so long as the weight itself provides proper buoyancy and stability to the electronic system 100 while it is in the body of fluid 103. Preferably, the weight provides a center of gravity for the electronic system 100.

Figure 6:
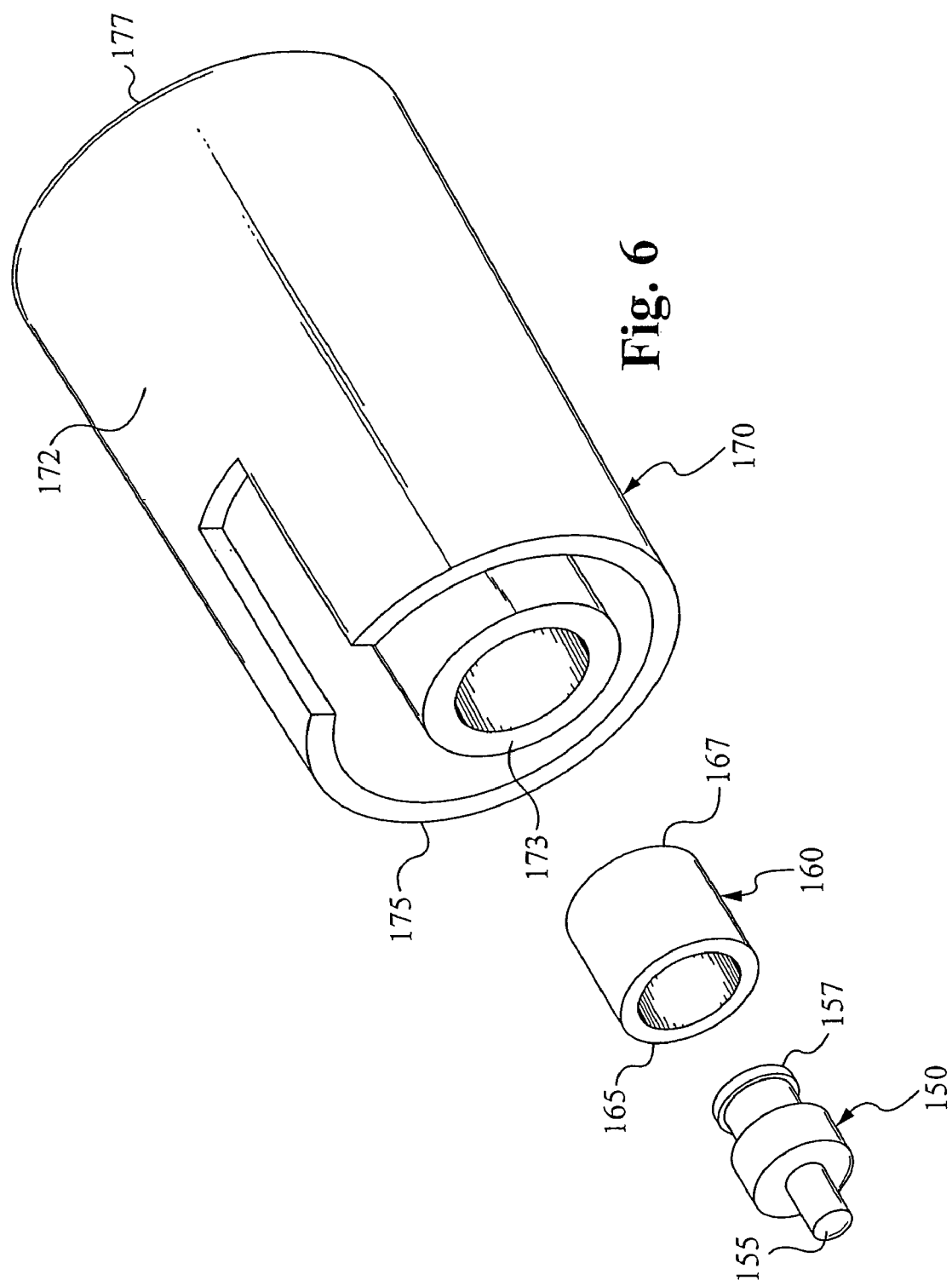
FIG. 6 is a schematic drawing of an overall isometric view of a sensor module, a BNC connector, and a BNC skirt, of the electronic system of FIG. 1A, in accordance with the preferred embodiment.
Figure 7A:
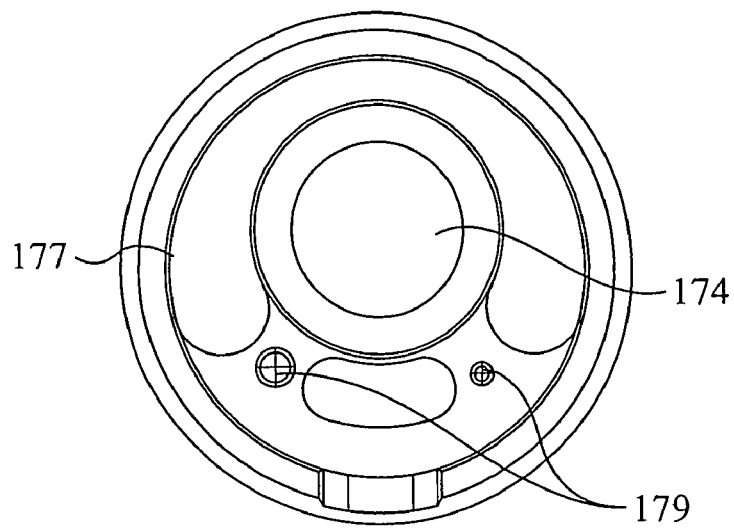
FIG. 7A is a schematic drawing of a side cross-sectional view of the sensor module of FIG. 6, in accordance with the preferred embodiment.
Figure 7B:
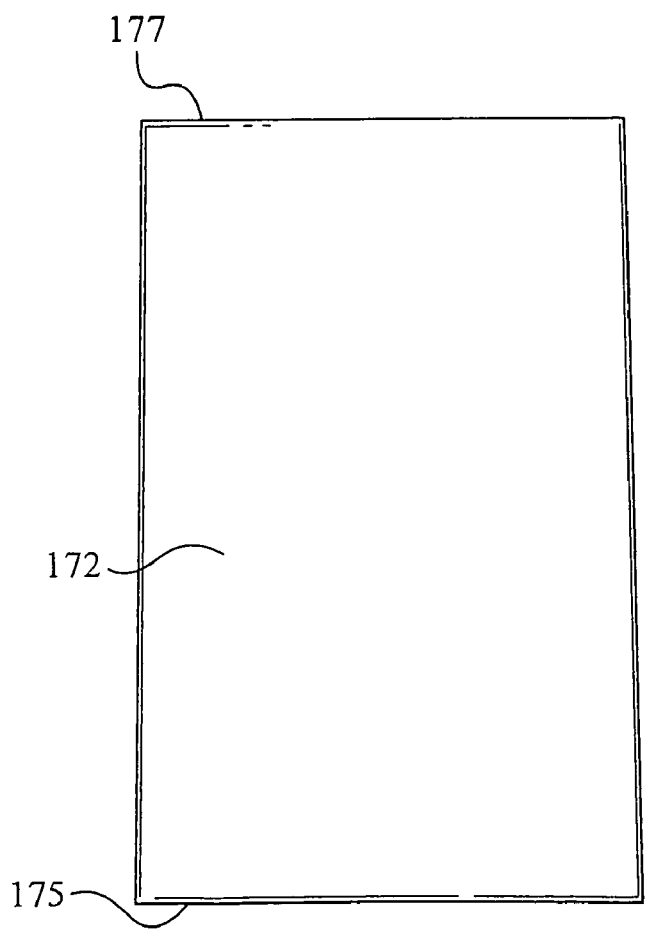
FIG. 7B is a schematic drawing of a top view of the sensor module of FIG. 6, in accordance with the preferred embodiment.
Figure 7D:
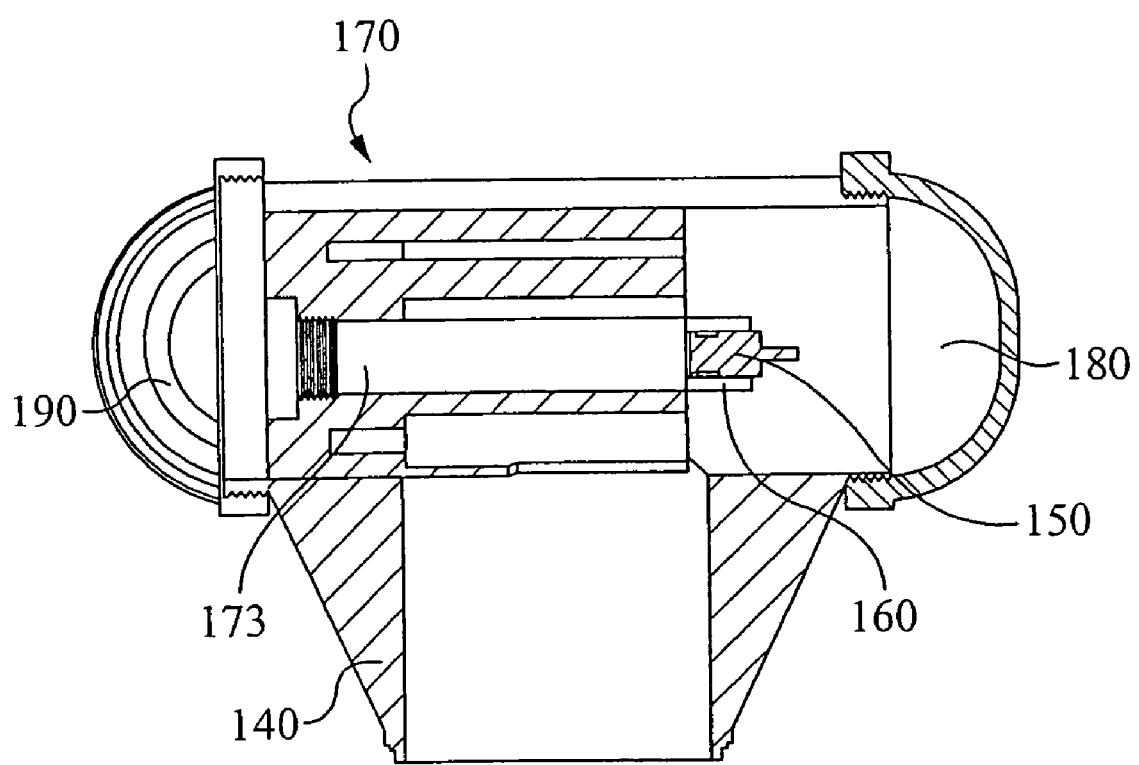
FIG. 7D is a cross sectional view of an axis cutting through the FIG. 7C to show an interior view of the sensor mount and the sensor module.
Figure 8A:
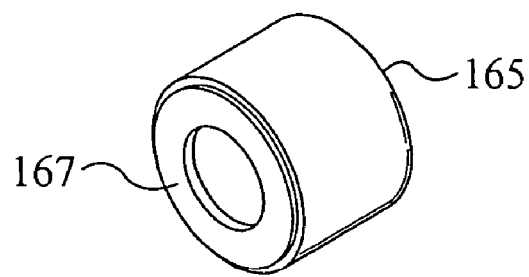
FIG. 8A is a schematic drawing of an isometric view of a BNC skirt for the electronic system of FIG. 1A, in accordance with the preferred embodiment.
Figure 8B:
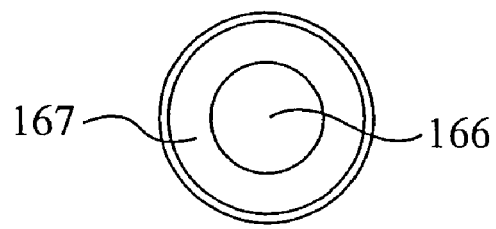
FIG. 8B is a schematic drawing of a side cross-sectional view of the BNC skirt of FIG. 8A.
Figure 8C:
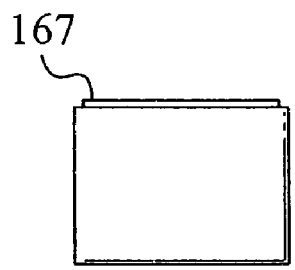
FIG. 8C is a schematic drawing of a front elevational view of the BNC skirt of FIG. 8A.

Referring to FIGS. 1, 6, 7C and 7C, as stated before, the sensor module 170 houses the sensor 173. The sensor module 170 preferably includes a housing 172, a sensor 173, a BNC connector 150, and a BNC skirt 160. The sensor module 170 is further housed by the sensor mount 140. Preferably, if the body of fluid 103 (FIG. 1C) is a pool, the sensor 173 is a replaceable screw-in pH reference junction, to calculate the pH and chlorine levels of the pool 103. The sensor 173 is for sensing and/or determining information about the body of fluid 103. Preferably, the sensor 173 is configured for determining chemistry information for a pool 103. The sensor 173 can be easily replaced by unscrewing the wetted cap 190 from an end of the sensor mount 170, removing the sensor 173 from the sensor module 170, putting in a new sensor 173 into the sensor module 170, and then screwing back on the wetted cap 190 on the end of the sensor mount 140 where the sensor module 170 is adjacent. Preferably, the sensor 173 is replaced on an annual basis. FIG. 7C shows the storage and wetted cap 180 and 190, in relation to the sensor mount 140 from a top perspective view. FIG. 7D shows the interior of the sensor mount 140 and the sensor module 170, by providing a cross-sectional view along the axis A-A of FIG. 7A.

Figure 9A:
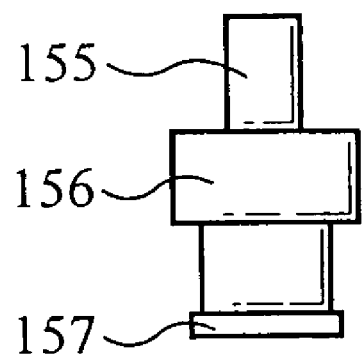
FIG. 9A is a schematic drawing of a front elevational view of a BNC connector for the electronic system of FIG. 1A, in accordance with the preferred embodiment.
Figure 9B:
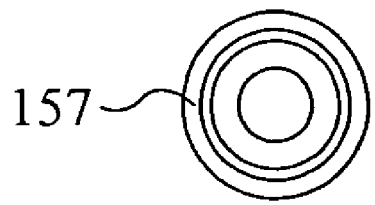
FIG. 9B is a schematic drawing of a side cross-sectional view of the BNC connector of FIG. 9A.

As described previously, a cable 130 extends from a transmitter board 115 (FIG. 1) through the first and second housing elements 110 and 120, to the sensor module 170 through an aperture in the sensor mount 140. The cable is coupled by a BNC connector 150, which is also coupled to the BNC skirt 160. The BNC connector 150 (FIGS. 9A and 9B) includes two ends, a first end 155 and a second end 157. The first end 157 of the BNC connector 150 is configured to couple with a first end 165 of the BNC skirt 160 (FIGS. 6, 8A, 8B, and 8C). The BNC connector skirt 160 similarly has two ends 167 and 165, one end 165 configured for coupling to the second end of 157 of the BNC connector (FIGS. 6 and 9A), while the other end 165 of the BNC connector skirt 160 is configured for coupling to sensor module 170. The BNC connector skirt 160 further includes a circular opening 166 (FIG. 8B) to couple with the second end 157 of the BNC connector 150.

Now referring to FIG. 7A, at a cross sectional side view, the sensor module 170 clearly includes the sensor 173. The sensor 173 is preferably made of metal. The sensor 173 is located on or about eighteen inches away from the top surface of the water. These eighteen inches provide a satisfactory water depth coverage for an electronic system 100 to be used in a pool, and it is intended to comply with standards set forth by the National Pool and Spa Institute. Preferably, the sensor 173 is a silver reference junction to calculate both pH and ORP (chlorine) levels of a pool. Preferably, the cable 130 (FIG. 1A) that couples the transmitter board 115 to the sensor 173 includes five cable wires. Two of the wires are for the coupling thermocouple (to measure temperature of the body of fluid 103), and the remaining three wires are for coupling the pH monitoring, ORP monitoring and one for the sensor 173 reference itself. Preferably, the first housing element 110 includes both the cable 130 and the BNC connector 150.

Figure 11A:
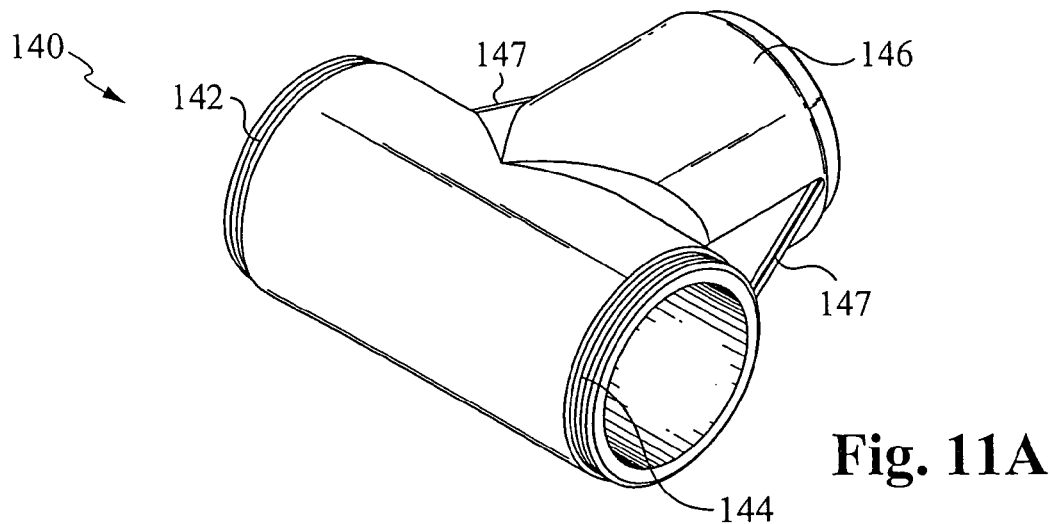
FIG. 11A is a schematic drawing of an overall isometric view of a sensor mount for the electronic system of FIG. 1A, in accordance with the preferred embodiment.
Figure 11B:
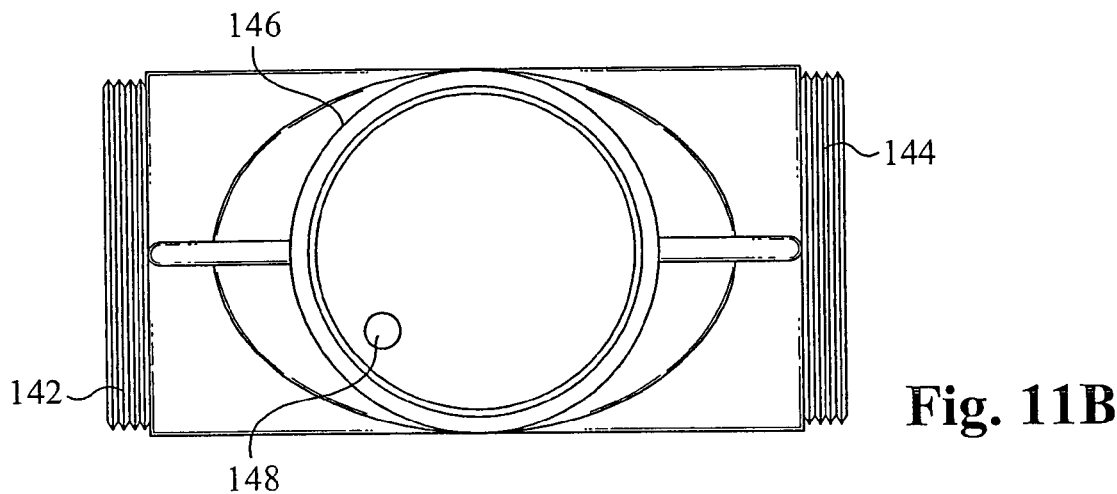
FIG. 11B is a schematic drawing of a side cross-sectional view of the sensor mount of FIG. 11A.
Figure 11C:
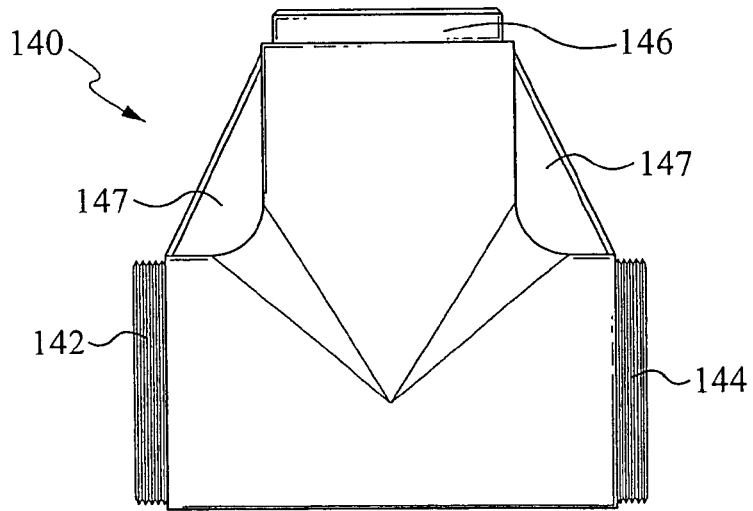
FIG. 11C is a schematic drawing of a front elevational view of the sensor mount of FIG. 11A.

Turning now to FIGS. 11A, 11B, and 11C, the sensor mount 140 houses the sensor module 170 (FIG. 1A). The sensor mount 140 provides three ends, a first end 142, a second end 144, and a third end 146. Preferably, as shown in FIG. 11, the sensor mount 140 includes threads at the first and second ends 142 and 144. The first and second ends 142 and 144 of the sensor mount 140 provide mounting for both the wetted cap 190 and the storage cap 180. The wetted cap 190 and the storage cap 180 are both detachable. Both the wetted cap 190 and the storage cap 180 are also configured such that each can fit either the first end 142 or the second end 144 of the sensor mount 140. Thus, the wetted cap 190 is configured to fit either the first end 142 or the second end 144 of the sensor mount 140. The storage cap 180 is similarly configured to fit either the first end 142 or the second end 144 of the sensor mount. The third end 146 (FIGS. 11A, 11B, and 11C) is coupled to the first housing element 110. Preferably, the third end 146 of the sensor mount is coupled to the first housing element 110 using an application of plastic glue, epoxy, sealant or the like to produce a weld-like coupling of the two.

FIG. 11B shows that an opening 148 is encircled by the third end 146 of the sensor mount 140. The opening 148 allows for the cable 130 (FIG. 1A) coupled to the electronic circuit 115 on one end to reach the sensor with the other end of the cable 130. Once the cable 130 couples both the electronic circuit 115 and the sensor, information can be transmitted by the cable 130 from the sensor to the electronic circuit 115. After the cable 130 is positioned through the opening 148, the opening 148 is sealed with an anti-moisture epoxy, glue or sealant Preferably, the electronic circuit 115 includes a transmitter board configured to transmit sensed information to a remote location, such as a receiver housed in a device 195 (FIG. 1A). The transmitter board 115 preferably is configured to transmit chemistry information through a digital radio connection or a custom radio interface connection. However, in other embodiments, the transmitter board 115 can transmit chemistry information through at least one of a wireless connection; such as WiFi, a cellular connection, a wired connection, an optical connection, or an infrared connection. The transmitter board 115 preferably transmits chemistry information to the device 195 every sixty seconds. The transmitter board 115 transmits preferably five data signals, namely identification, battery voltage, temperature of the body of fluid 103, pH level of the body of fluid 103, and ORP/chlorine level of the body of fluid 103. FIG. 11C further shows that the sensor mount 140 includes a pair of support elements 147. An overall view of the configuration of the sensor mount 140 in relation to the wetted cap 190, the storage cap 180, and the first housing element 110 in the assembled electronic system 100 is shown in FIG. 14.

During manufacturing, a sensor 173 is installed inside the sensor mount 140 with glass balls that need to be kept moist. A moist sponge foam (dipped in a solution having a pH of 4) is then placed with the sensor 173, and the storage cap 180 is placed on the end nearest to the sensor module containing the sensor. The storage cap 180 helps to prevent evaporation to keep the sponge foam moist, and to preserve the sensor during shipping. The storage cap 180 is then screwed on or threaded on to an end of the sensor mount 140 nearest to the sensor. If the storage cap 180 is placed on the first end 142 of the sensor mount 140 (FIGS. 11A, 11B, and 11C), then the wetted cap 190 is placed on the second end 144 opposite of the first end 142 of the sensor mount 140.

Figure 12A:
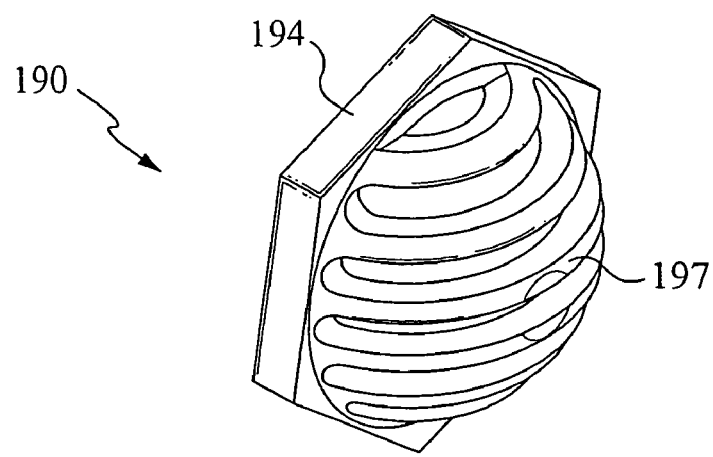
FIG. 12A is a schematic drawing of a isometric view of a wetted cap for the electronic system of FIG. 1A, in accordance with the preferred embodiment.
Figure 12B:
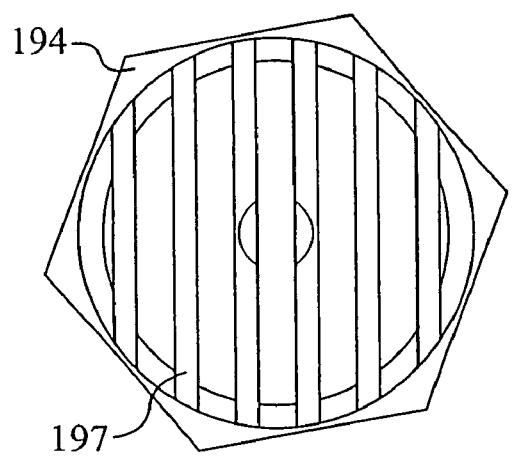
FIG. 12B is a schematic drawing of a side cross-sectional view of the wetted cap of FIG. 12A.
Figure 12C:
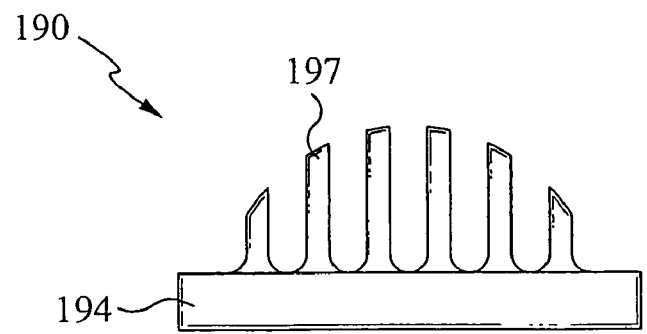
FIG. 12C is a schematic drawing of a side elevational view of the wetted cap of FIG. 12A.

Several views of the wetted cap 190 are provided in FIGS. 12A, 12B, and 12C. The wetted cap 190 includes a slotted top 197 and a hexagon-shaped end 194. Inside the hexagon-shaped end 194 is a plurality of circular threads (not shown), which permit the wetted cap 190 to be threaded on, twisted, turned, screwed, or otherwise mounted onto one of the two ends 142 or 144 of the sensor mount 140. When the electronic system 100 is shipped to a customer, the wetted cap 190 is initially not on the end of the sensor mount 140 nearest to the sensor. Instead, the storage cap 180 is nearest to the sensor, thus ensuring that the sensor is not exposed to outside elements while the electronic system 100 is shipped. Once the electronic system 100 has reached its end customer, the customer can then swap or switch the wetted cap 190 with the storage cap 180, thereby mounting the wetted cap 190 near to the sensor 173, such that the sensor 173 can be exposed to the body of fluid 103 once the electronic system 100 is placed in the body of fluid 103.

Figure 13A:
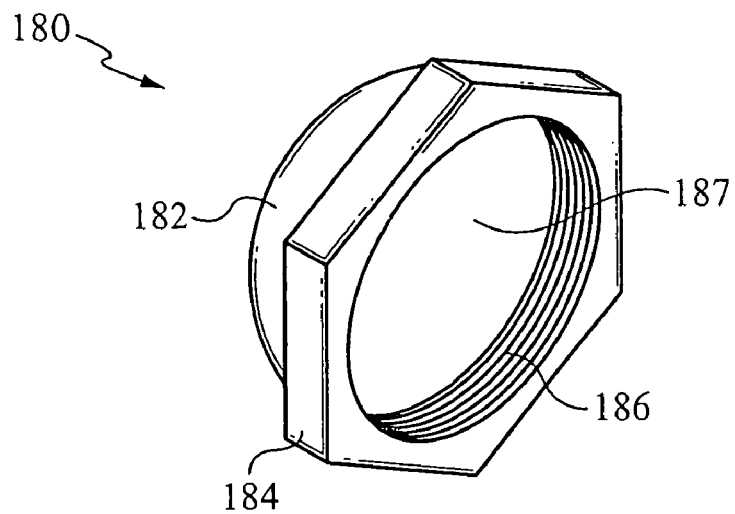
FIG. 13A is a schematic drawing of an isometric view of a storage cap for the electronic system of FIG. 1A, in accordance with the preferred embodiment.
Figure 13B:
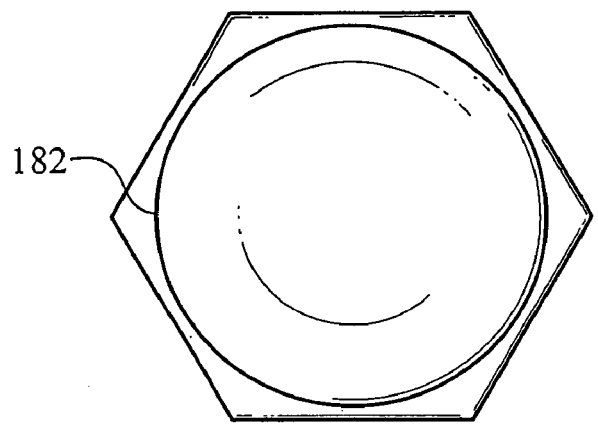
FIG. 13B is a schematic drawing of a side cross-sectional view of the storage cap of FIG. 13A.
Figure 13C:
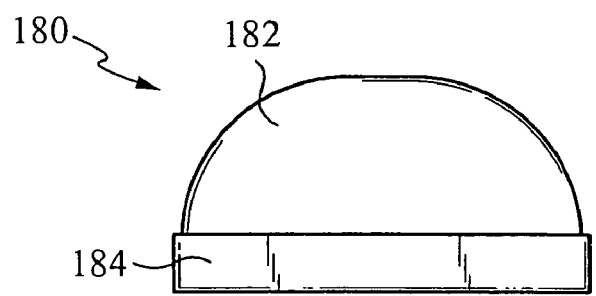
FIG. 13C is a schematic drawing of a side view of the storage cap of FIG. 13A.

The storage cap 180 is noticeably different in appearance from the wetted cap 190. As shown in FIGS. 13A, 13B, and 13C, the storage cap 180 preferably includes a rounded top 182 and a hexagon-shaped end 184. Inside the hexagon-shaped end 184 is a plurality of threads 186, which allow for the storage cap 180 to be threaded on, twisted, turned, screwed, or otherwise mounted onto one of the two ends 142 and 144 of the sensor mount 140. Preferably, the storage cap 180 is mounted on the end of the sensor mount 140 opposite to the wetted cap 190. Preferably, the storage cap 180 includes an aperture or opening 186 which is surrounded by the hexagon-shaped end 184. As mentioned previously, the storage cap 180 is placed initially during manufacturing near the sensor, to protect the sensor with a foam sponge, as discussed previously. Once the electronic system 100 reaches its customer, the customer can then unscrew both the storage cap 180 and the wetted cap 190 from opposite ends of the sensor mount 140. The customer can then swap, exchange, or switch the storage cap 180 and the wetted cap 190, such that the storage cap 180 is far removed from the sensor and the wetted cap 190 is nearby the sensor to expose it to the body of fluid 103 once the electronic system 100 is placed in the body of fluid 103.

Once the customer has switched the storage cap 180 and the wetted cap 190, and the handheld device 195 (FIG. 1A) has gone through the initial set up, the electronic system 100 is ready to be placed in the body of fluid 103 (FIG. 1C). As mentioned previously, in FIG. 1C, the electronic system 100 includes an electronic circuit 115 which preferably is a transmitter board. The transmitter board 115 is configured to transmit information to a remote receiver preferably housed in a device 195. Preferably, the electronic system 100 is configured to allow the sensor 173 to sense or determine chemistry information of a body of fluid 103. Preferably, the body of fluid 103 is a pool. Once the sensor determines chemistry information for the body of fluid 103, the chemistry information is transmitted from the sensor to the transmitter board via the cable 130. Upon receipt of the chemistry information sensed by the sensor 173, the transmitter board 115 transmits the chemistry information using short wave radio or wireless connection to the device 195. Preferably, the chemistry information is one alkalinity, pH level, temperature, calcium hardness, total hardness, dissolved solids, and a sanitizer of the body of water 103 and a combination of at least two thereof.

Preferably, the device 195 is to remotely monitor a body of fluid 103. The device 195 includes a control circuit (not shown) and a display 199. Preferably, the display 199 is a LCD display. The display 199 is for displaying the chemistry information received and processed by the control circuit. Preferably, the control circuit is a receiver to receive transmitted chemistry information from the transmitter board 115 (FIG. 1A) in the electronic system 100. Further, the control circuit further comprises a microprocessor. Preferably, during manufacturing, the control circuit is paired with a designated transmitter board 115 in a designated electronic system 100, such that the control circuit can receive information only from the designated transmitter board 115. The designated transmitter board 115 likewise has been programmed to transmit only to the control circuit in the device 115 that has been paired to the transmitter board 115. Transmission is preferably only one way from the transmitter board 115 to the control circuit of the device 115. By pairing a designated transmitter board 115 with a designated control circuit, cross talk from neighboring similar electronic systems 100 and devices 195 is prevented.

Preferably, the device 195 is a device configured to use an electrical wall outlet as its power supply. For instance, the device 195 can have an adapter that is connected to connect to the electrical outlet. Alternatively, the device 195 can be a handheld device and have a separate power supply, such as a rechargeable battery. Here, the device 195 can have a separate cradle mounted on a wall and plugged into a wall outlet. This enables the device 195 to recharge its battery when the device 195 is placed in the cradle for charging on a periodic basis. The advantage of this embodiment is that the cradle increases the convenience and portability of the device 199.

Preferably, the device 195 includes a user input interface 198 (FIG. 16A), such as a plurality of keypads or buttons. The control circuit in the device 195 further includes a software program that runs through an initial set up menu that will be displayed on the display 199 when the device 195 is powered on for the first time. With the help of the set up menu of the device 195, the user can input information about the body of fluid 103 being monitored by the device 195. Using the set up menu, the device 195 will display set up inquiries on the display 199. For instance, the user will be asked to input the dimensions or volume of the body of fluid 103 being monitored. In the preferred embodiment, the user will be asked to input the dimensions of the pool 103 being monitored. The user can then input the dimensions or volume of the pool using the user input interface 198. Also, the user will be asked if the pool is salt water or tap water, and what is the volume of the pool. Once the user inputs this information using the user input interface 198, the device 195 will further display questions to what pool chemicals does the user have on hand. The user will input information indicating whether he has solid chlorine, granulated chlorine, liquid chlorine, and/or an ionizer at his disposal. Once the device 195 completes its initial set up, the device 195 will begin monitoring the body of fluid 103 with the help of the electronic system 100 (FIG. 1A) that is preferably floating in the body of fluid 103.

Figure 16A:
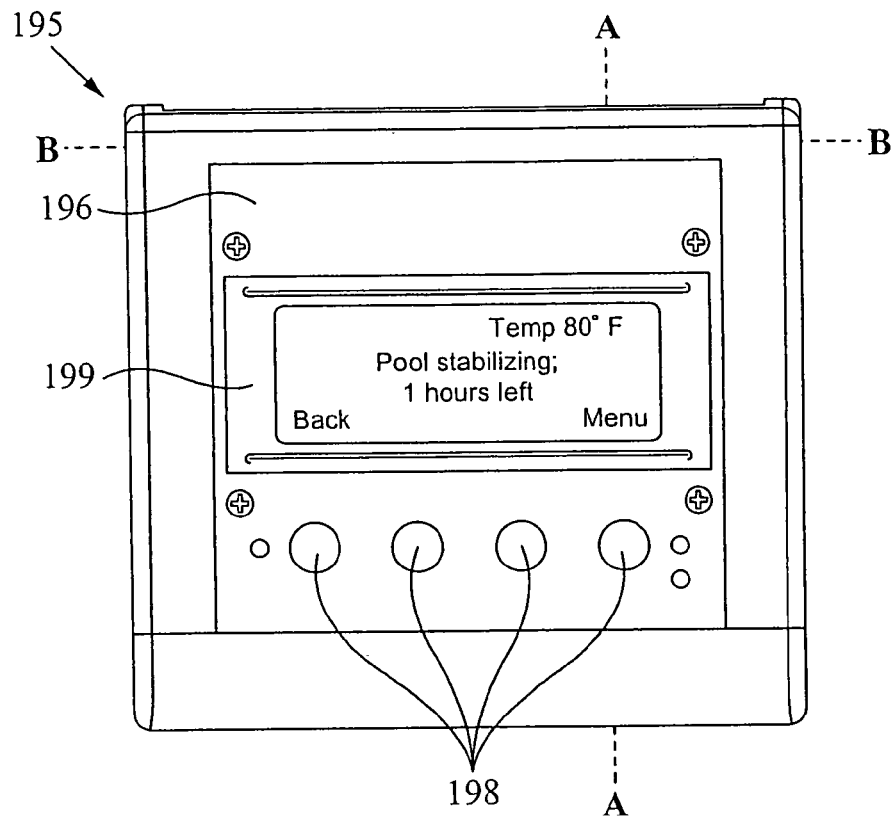
FIGS. 16A, 16B, 16C, 16D, and 16E are schematic drawings of a device for the electronic system, in accordance with the preferred embodiment of the present invention.

FIG. 16A shows a top isometric view of one exemplary embodiment of the device 195, which includes the display 199 and the user input interface 198. FIG. 16A is exemplary only in showing that the user input interface 198 includes four menu buttons. It will be apparent to those skilled in the art that the user input interface 198 can take on any number of configurations, including but not limited to alphanumeric keypads, soft function keys, menu buttons, touch pads, scrolling bar mechanism, and the like. Preferably, the display 199 is mounted on a top cover 196 that covers a PC board, which will later be discussed.

Figure 16B:
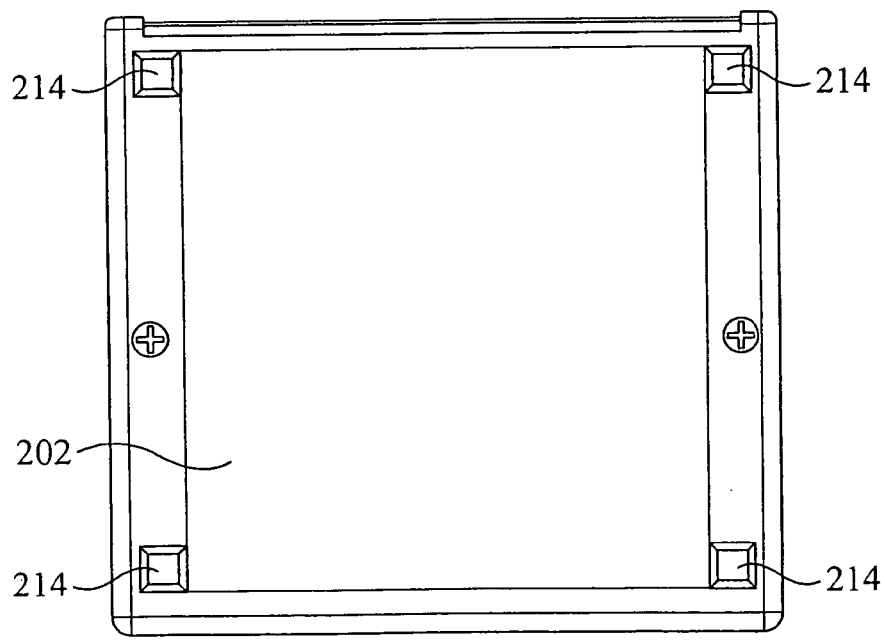
Figure 16C:
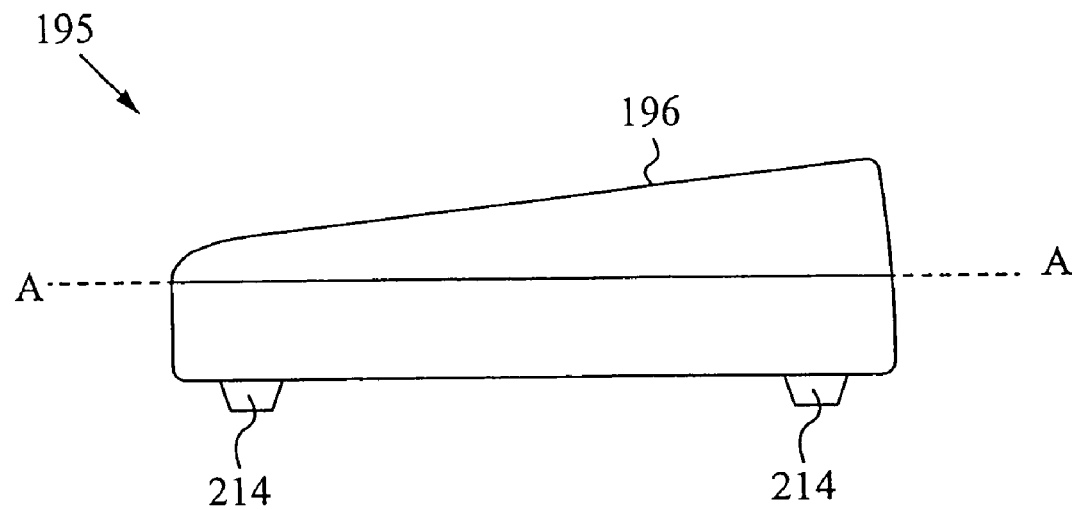
Figure 16D:
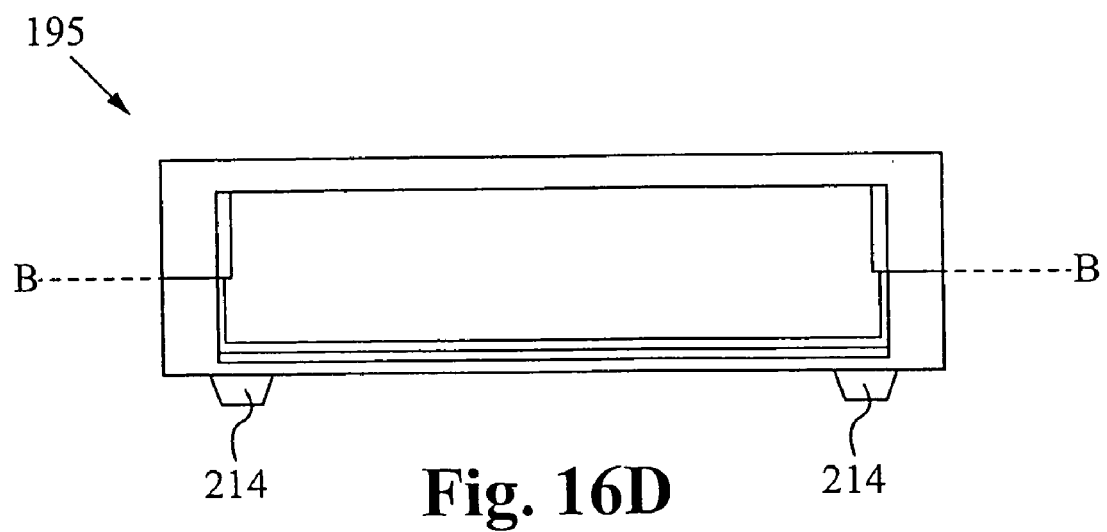
Figure 16E:
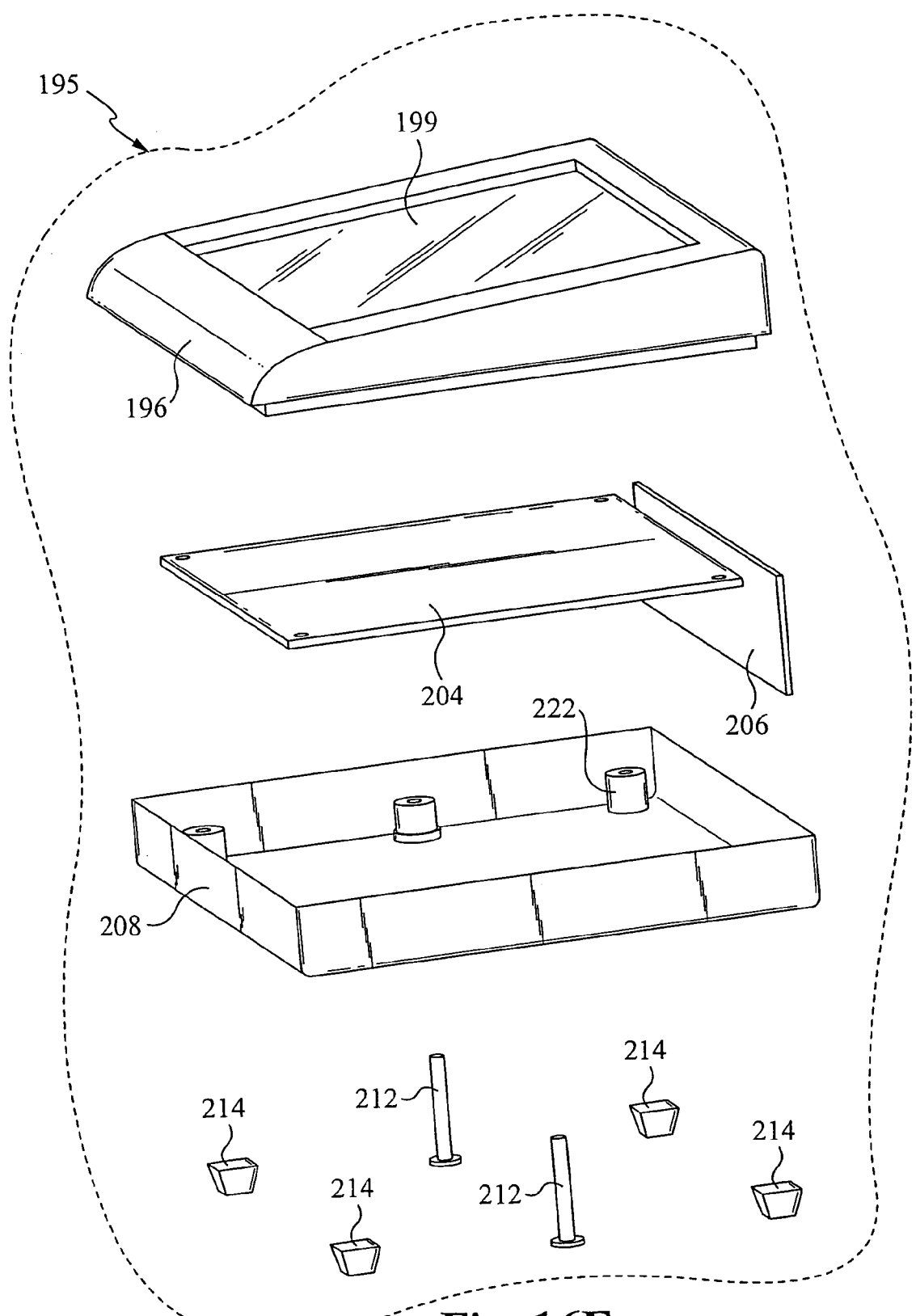

FIG. 16B shows a rear isometric view of the device 195 which includes a bottom cover 202. The bottom cover 202 preferably includes four rubber feet 214, which protects the bottom cover 202 from wear. FIG. 16C shows the device 195 of FIG. 16A from a side view through the A-A axis, while FIG. 16D shows the device 195 of FIG. 16A from a side view through the B-B axis. Finally, FIG. 16E shows the device 195 disassembled. Preferably, the device 195 includes the top cover 196 having a display 199, a PC board 204, a rear panel 206, a bottom cover 208 having mounting supports 222, screws 212, and four rubber feet 214.

Figure 17:
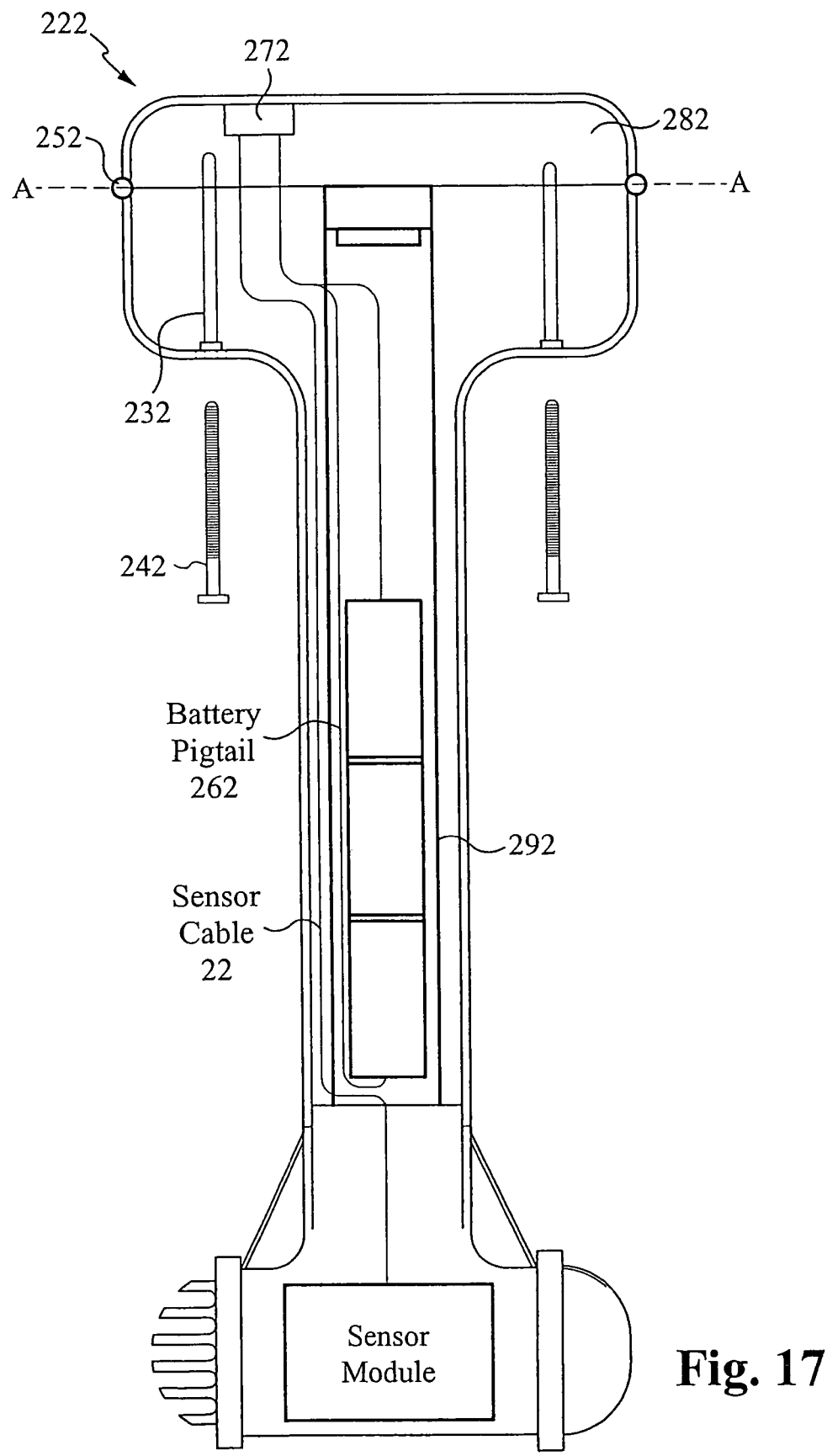
FIG. 17 is a schematic drawing of an isometric view of an electronic system, in accordance with an alternative embodiment of the present invention.

FIG. 17 shows an alternative embodiment of the electronic system 100 (FIG. 1A). FIG. 17 is similar to FIG. 14 except for the following differences. The electronic system 222 of FIG. 17 includes a first housing element 282 and a second housing element 292, but the first and second housing elements 282 and 292 are detachable and must be hermetically sealed by manually coupling them using o-rings 252 and screws 242. The screws 242 are configured to be screwed into apertures 232 in the electronic system 222. Thus, unlike the preferred embodiment shown in FIG. 14, the electronic system 222 of FIG. 17 does not hermetically seal the second housing element 292 to the first housing element 282 by a plastic glue, epoxy or any other anti-moisture sealant. Instead, manual coupling of the first and second housing elements 282 and 292 is required for the electronic system 222. Also, a receiver compartment 272 is coupled to a sensor cable 22 and a battery pigtail 262. The sensor cable 22 is similar to the cable 130 of the preferred embodiment of the electronic system 100. However, since the first and second housing elements 282 and 292 of the electronic system 222 in FIG. 17 are detachable, the sensor cable 22 and the battery pigtail 262 can be exposed to external conditions when the first and second housing elements 282 and 292 are decoupled.

Figure 18:
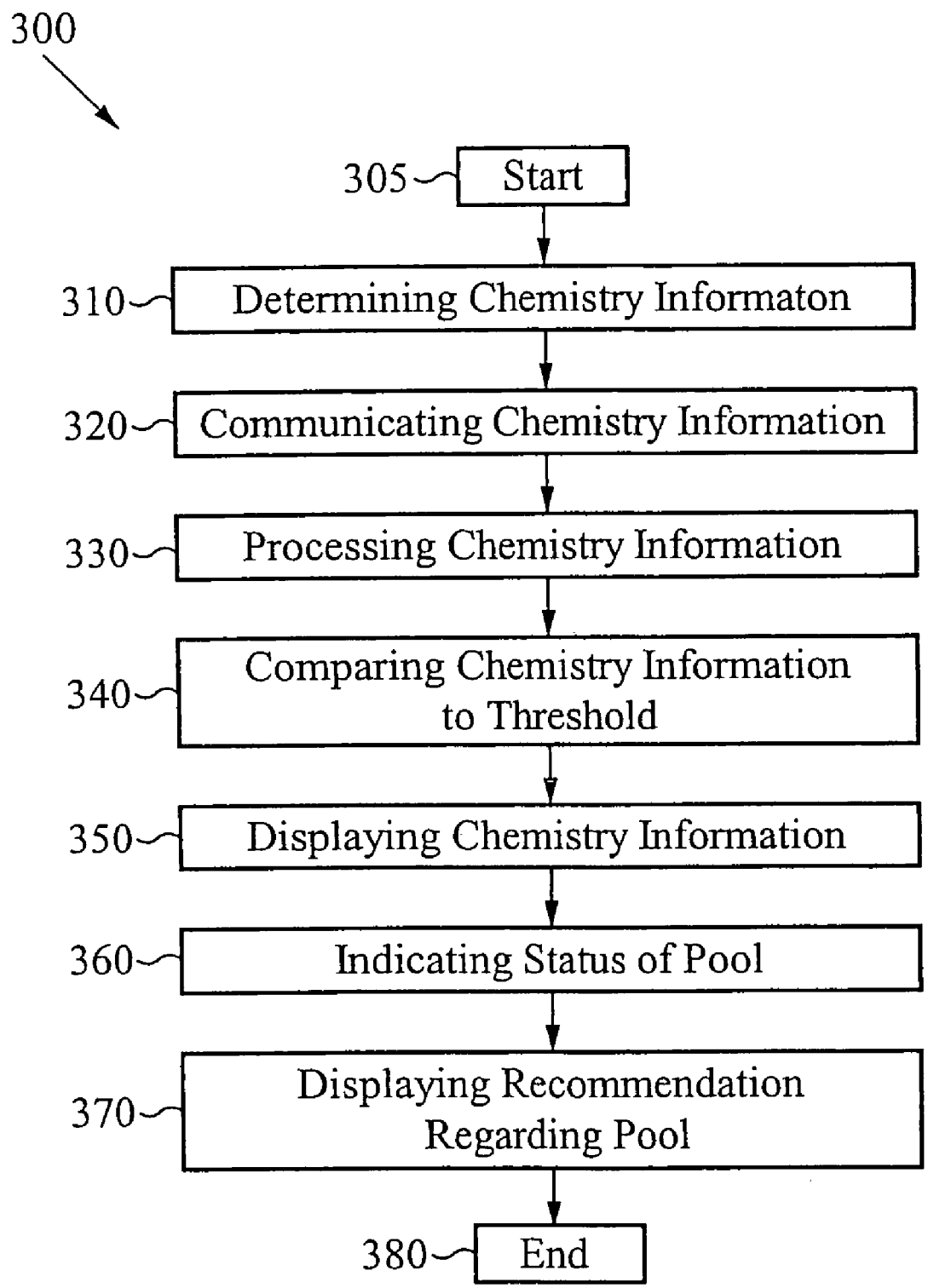
FIG. 18 is a flow chart diagram showing a sequence of steps of a method for monitoring chemistry information for a pool, in accordance with the preferred embodiment.

FIG. 18 shows a flow chart diagram of the steps involved in a method 300 for monitoring a body of fluid 103 (FIG. 1C), beginning with a start step 305. At a step 310, chemistry information of the body of fluid must be determined. Preferably, chemistry information is determined using a sensor submerged in the body of fluid 103. Next, at an optional step 320, the chemistry information that was determined can be communicated or relayed. Preferably, the chemistry information is communicated to a control circuit that acts as a receiver. At the step 330, the chemistry information is processed, preferably by a control circuit having a microprocessor. At the step 340, the processed chemistry information is compared to one or more programmable thresholds. At the step 350, the processed chemistry information is displayed, preferably using a display on a handheld device. At the step 360, a status of the body of fluid 103 (FIG. 1C) is indicated. Preferably, the status is one of a safe status, a cautionary status or an unsafe status. Preferably, if the body of fluid 103 is a pool, a safe status means that the pool is balanced and safe to enter, whereas an unsafe status means that the pool is unbalanced and unsafe to enter. An unsafe status means that the body of fluid 103 needs immediate attention and maintenance. A cautionary status means that a threshold will soon be reached, and that the body of fluid 103 needs maintenance soon. Based on the status and processed chemistry information of the body of fluid 103, a recommendation will be provided and displayed at a step 370. For example, the control circuit determines that chlorine is lacking in the body of fluid 103. Then, at the step 370, a recommendation for chlorine to be added to the body of fluid 103 will be displayed. Finally, at the step 380, the method 300 ends.

Figure 19:
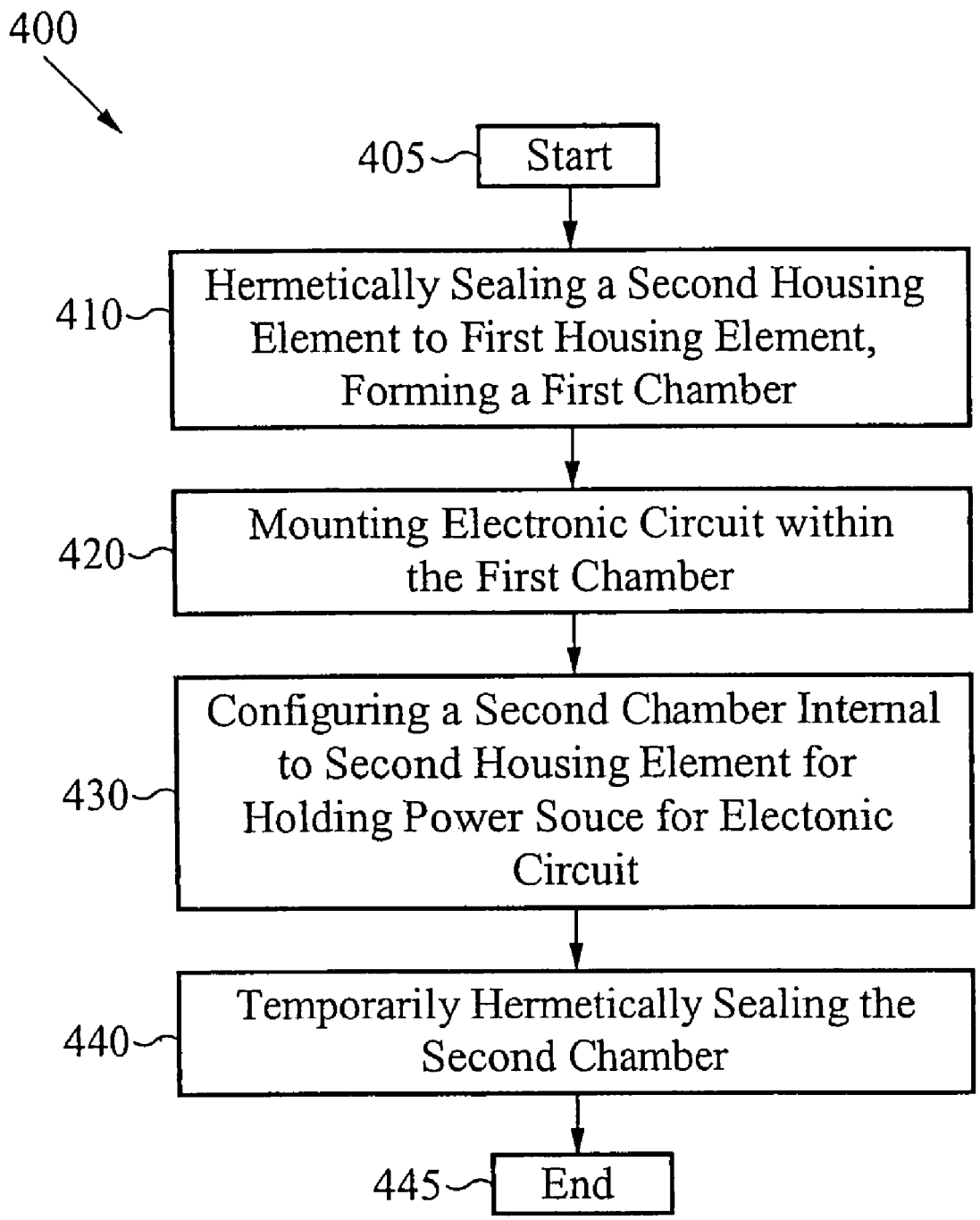
FIG. 19 is a flow chart diagram showing a sequence of steps of a method for manufacturing the electronic system of FIG. 1A, in accordance with the preferred embodiment.

FIG. 19 shows a flow chart diagram of the method 400 to manufacture an electronic system having a first housing element and a second housing element, where the electronic system is for use in a body of fluid. At a step 405, the method 400 begins. At a step 410, the second housing element is hermetically sealed to the first housing element, thus forming a first chamber there between. Preferably, the first and second housing elements are hermetically sealed using a sealant, glue, epoxy, and the like. At a step 420, an electronic circuit is mounted within the first chamber. At a step 430, a second chamber internal to the second housing element is configured for holding a power source for the electronic circuit. Then, at a step 440, the second chamber is temporarily hermetically sealed. Preferably, the second chamber is sealed using a plug. Finally, the method 400 ends at a step 445.

Reference has been made in detail to the preferred and alternative embodiments of the invention, examples of which are illustrated in the accompanying drawings. While the invention has been described in conjunction with the preferred embodiments, it will be understood that they are not intended to limit the invention to these embodiments. On the contrary, the invention is intended to cover alternatives, modifications and equivalents, which may be included within the spirit and scope of the invention. Furthermore, in the previous detailed description of the present invention, numerous specific details have been set forth in order to provide a thorough understanding of the present invention. However, it should be noted that the present invention may be practiced without these specific details. In other instances, well known methods, procedures and components have not been described in detail as not to unnecessarily obscure aspects of the present invention.

What is claimed is:

1. An electronic system for use in a body of fluid comprising:
    a first housing element having a first upper portion and a first hollow member extending from the first upper portion, the first hollow member comprising a first top end adjacent to the first upper portion and a first bottom end opposite the first top end;
    a second housing element having a second upper portion and a second hollow member extending from the second upper portion, the second hollow member comprising a second top end adjacent to the second upper portion and a second bottom end opposite the second top end, the second housing element being hermetically sealed to the first housing element forming a first chamber there between, wherein an electronic circuit is mounted within the first chamber;
    a second chamber internal to the second housing element configured for holding a power source for the electronic circuit;
    means for temporarily hermetically sealing the second; and
    a sensor housed within a sensor housing, the sensor housing coupled to the first bottom end, the sensor configured to sense information about the body of fluid,
    wherein the first and second upper portions are configured to float above the body of fluid, and the first bottom end, the second bottom end, the sensor housing, and the sensor are configured to be disposed under the body of fluid while the first and second upper portions are floating above the body of fluid.

2. The electronic system of claim 1, wherein the electronic system is floatable in the body of fluid.

3. The electronic system of claim 1, wherein means for temporarily hermetically sealing the second chamber comprises a detachable plug coupled to the second housing element.

4. The electronic system of claim 1, wherein the power source comprises a battery pack.

5. The electronic system of claim 1, wherein the system is further configured to be tethered.

6. The electronic system of claim 1, wherein the body of fluid comprises a pool.

7. The electronic system of claim 1, further comprising a cable that couples the electronic circuit to the sensor, the cable being housed inside the first hollow member and passing through the first bottom end to the sensor.

8. The electronic system of claim 1,
    wherein the sensor is coupled to the electronic circuit and at least one of the first and second housing elements.

9. The electronic system of claim 8, further comprising a cable coupling the sensor to the electronic circuit.

10. The electronic system of claim 9, wherein the cable is hermetically enclosed within the first chamber.

11. The electronic system of claim 1, wherein the electronic circuit comprises a transmitter configured to transmit information determined from the sensed information about the body of fluid to a remote location.

12. The electronic system of claim 11, wherein the sensed information is chemistry information.

13. The electronic system of claim 11, wherein the transmitter is configured to transmit the determined information to a remote location every predetermined amount of time.

14. The electronic system of claim 1, wherein:
    the second hollow member has a smaller diameter than the first hollow member;
    the second hollow member is disposed inside the first hollow member; and
    the first hollow member covers the second hollow member.

15. The electronic system of claim 14, wherein the sensor is disposed about eighteen inches away from the top surface of the body of fluid.

16. The electronic system of claim 14, further comprising a cable that couples the electronic circuit to the sensor, the cable being housed inside the first hollow member and passing through the first bottom end to the sensor.

* * * * *